(12) United States Patent
Hashiba et al.

(10) Patent No.: US 9,370,338 B2
(45) Date of Patent: Jun. 21, 2016

(54) ULTRASOUND DIAGNOSIS DEVICE

(75) Inventors: Kunio Hashiba, Tokyo (JP); Hideki Yoshikawa, Hino (JP); Tatsuya Hayashi, Kashiwa (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 201 days.

(21) Appl. No.: 13/701,838

(22) PCT Filed: May 25, 2011

(86) PCT No.: PCT/JP2011/061952
§ 371 (c)(1),
(2), (4) Date: Dec. 4, 2012

(87) PCT Pub. No.: WO2011/152260
PCT Pub. Date: Dec. 8, 2011

(65) Prior Publication Data
US 2013/0144172 A1    Jun. 6, 2013

(30) Foreign Application Priority Data

Jun. 4, 2010 (JP) .................................. 2010-128405

(51) Int. Cl.
 A61B 8/06  (2006.01)
 A61B 8/08  (2006.01)
 G01S 7/52  (2006.01)
 G01S 15/89  (2006.01)
 A61B 8/00  (2006.01)
 A61B 8/14  (2006.01)

(52) U.S. Cl.
CPC . *A61B 8/481* (2013.01); *A61B 8/08* (2013.01); *A61B 8/5269* (2013.01); *G01S 7/52038* (2013.01); *G01S 7/52039* (2013.01); *G01S 15/895* (2013.01); *G01S 15/8963* (2013.01); *A61B 8/0891* (2013.01); *G01S 7/52077* (2013.01)

(58) Field of Classification Search
None
See application file for complete search history.

(56) References Cited

U.S. PATENT DOCUMENTS 5,577,505 A  * 11/1996 Brock-Fisher et al. ....... 600/458
6,319,203 B1 * 11/2001 Averkiou ...................... 600/443
6,494,841 B1   12/2002 Thomas et al.
7,037,265 B2 *  5/2006 Hao et al. ...................... 600/447

FOREIGN PATENT DOCUMENTS

JP    2002-336248    11/2002
JP    2004-504911    2/2004
WO    WO 02/10795 A2  2/2002

* cited by examiner

*Primary Examiner* — Long V Le
*Assistant Examiner* — Kevin Pontius
(74) *Attorney, Agent, or Firm* — Baker Botts L.L.P.

(57) ABSTRACT

Disclosed is an ultrasound diagnosis device for creating an ultrasound image with a high contrast-to-tissue ratio. Said device sends a transmission pulse to the subject, uses an ultrasound probe to receive echoes reflected from an ultrasound contrast agent injected into the subject, and forms an image. The transmission pulse is sent such that nonlinear interactions between the constituent frequency components of said transmission pulse, as a result of the acoustic nonlinearity of the subject, do not produce sum and difference components in the frequency sensitivity range of the ultrasonic probe as the transmission pulse propagates across the subject.

9 Claims, 12 Drawing Sheets

FIG. 9
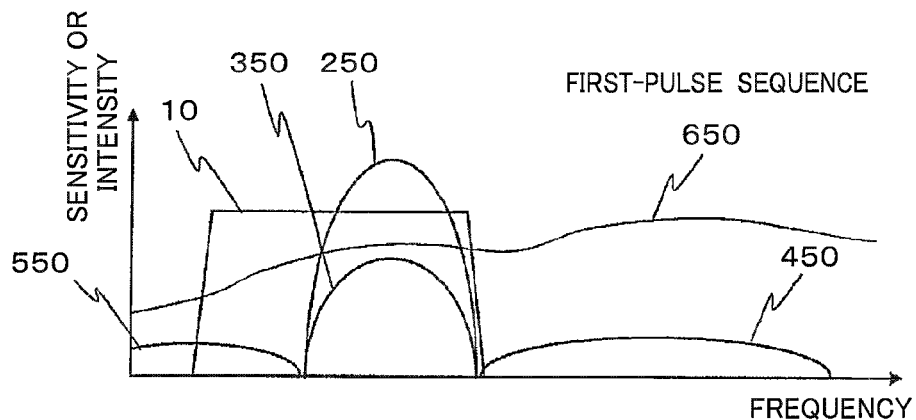
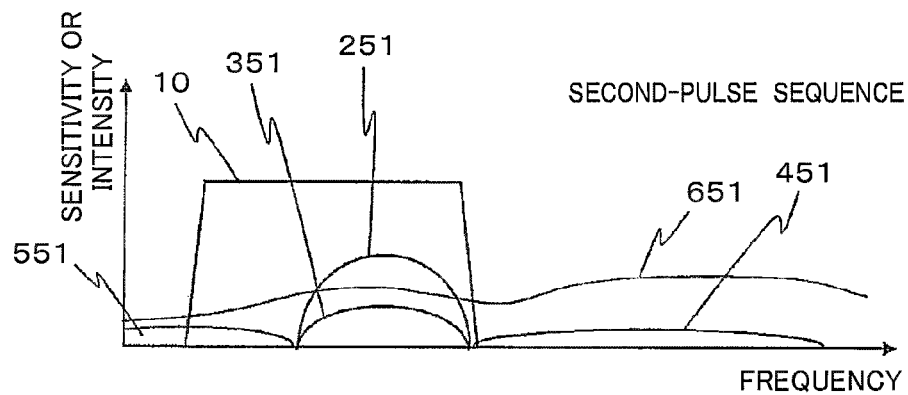
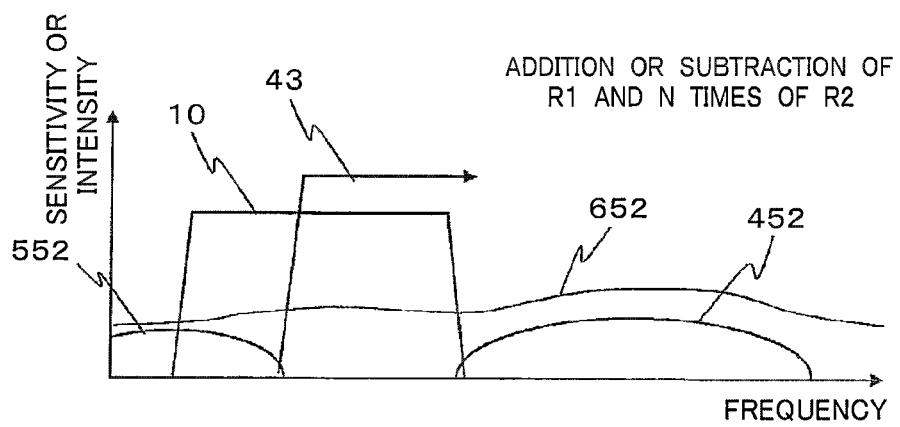

| | CONVENTIONAL (a) | OUR METHOD (b) | EFFECT (a/b) |
|---|---|---|---|
| CONTRAST ECHO COMPONENT (C) | −157.36dB | −162.06dB | −4.70dB |
| NONLINEAR TISSUE ECHO COMPONENT (T) | −25.65dB | −46.38dB | −20.73dB |
| IMPROVEMENT OF CTR | | | 16.03dB |

ULTRASOUND DIAGNOSIS DEVICE

TECHNICAL FIELD

The present invention relates to an ultrasound diagnosis device, and specifically, to an ultrasound diagnosis device that images an ultrasound contrast agent injected into a biological body.

BACKGROUND ART

An ultrasound diagnosis device is a device that transmits an ultrasound pulse from an ultrasound probe into a biological body and receives an ultrasound echo scattered or reflected from the biological body using the ultrasound probe to perform various signal processings on the received ultrasound echo to obtain a body tissue B-mode image or a blood flow image and is widely used for medical diagnosis.

One of imaging methods of the ultrasound diagnosis device is an ultrasound contrast imaging using an ultrasound contrast agent. The ultrasound contrast imaging is a method that intravenously injects an drug formulation, which is obtained by stabilizing microbubbles having a micron size order using some method, as an ultrasound contrast agent into the biological body in advance to perform the ultrasound imaging. This method has been widely used to diagnose a disease of blood vascular system such as malignant tumor or infarction.

As for ultrasound wave of several MHz which is mainly used for ultrasound diagnosis, the ultrasound contrast agent in forms of microbubbles shows significantly high nonlinear response. Therefore, a nonlinear component of the ultrasound echo in the ultrasound contrast imaging includes lots of ultrasound echoes from the ultrasound contrast agent. There is an attempt that the ultrasound echo of the nonlinear component is extracted to form an image to visualize a vascular structure. The related art will be described in detail with reference to FIGS. 2 and 3.

FIG. 2 is a frequency spectrum illustrating both a frequency band of a transmit pulse and a received echo of an ultrasound wave and a sensitivity frequency band of an ultrasound probe in the related art.

If the transmit pulse 200 is transmitted from the ultrasound probe of the probe sensitivity band 10 to perform the imaging by the ultrasound contrast imaging, a linear tissue echo component 300, nonlinear tissue echo components 400 and 500, and an contrast echo component 600 are received so as to be included in the received echo. Here, the linear tissue echo component 300 is an echo received from a tissue by a fundamental component of the transmit pulse 200. Further, the nonlinear tissue echo component 400 is a received echo from a tissue by a second harmonic wave component (sum frequency component of a frequency component of the fundamental wave included in the transmit pulse 200) which is produced during the process of propagating the transmit pulse 200 in the biological body. Like the nonlinear tissue echo components 400, the nonlinear tissue echo component 500 is a received echo from a tissue by a nonlinear component which is produced during the process of propagating the transmit pulse 200 in the biological body and generated by a difference-frequency component of the frequency components of the fundamental wave included in the transmit pulse 200.

The contrast echo component 600 is widely distributed with a high acoustic intensity in a frequency range of the probe sensitivity band 10 by a strong nonlinear response of the contrast agent. However, the nonlinear tissue echo components 400 and 500 are generated by a nonlinear acoustic effect (waveform distortion or accumulation thereof) of the biological tissue. Therefore, a ratio of the intensities of the nonlinear tissue echo components 400 and 500 to the linear tissue echo component 300 is low. Therefore, by processing a frequency band where the nonlinear tissue echo components 400 are distributed using a filter represented by a pass band 40, a frequency component in which only an intensity of the contrast echo component 600 is comparatively strong may be extracted so that the imaging is performed with a signal of the extracted frequency component. By doing this, it is possible to visualize a vascular image which is not comparatively buried in the signal from the tissue. In this related art, it is required to sufficiently separate the frequency band in which the linear tissue echo components 300 are distributed and the frequency band in which the nonlinear tissue echo components 400 are distributed and a lower frequency band of the probe sensitivity band 10 is not necessarily used for imaging.

Next, another related art will be described with reference to FIG. 3.

FIG. 3 illustrates a method that adds a received echo R1 obtained by a first transmit pulse 210 and a received echo R2 obtained by a second transmit pulse 211 produced by positive-to-negative inversing the first transmit pulse 210 and transmitted on the same scanning line as the first transmit pulse 210 to remove an echo reflected from the tissue by a fundamental component of the transmit pulse and is referred to as pulse inversion technique.

The received echo R1 from the first transmit pulse 210 includes a linear tissue echo component 310 from a tissue by a fundamental component of the transmit pulse 210, nonlinear tissue echo components 410 and 510 from a tissue by a nonlinear component of sum frequency component and difference-frequency component generated in the process of propagation of the first transmit pulse 210 in a biological body, and a contrast echo component 610. Further, the received echo R2 from the second transmit pulse 211 includes a linear tissue echo component 311 from a tissue by a fundamental component of the transmit pulse 211, nonlinear tissue echo components 411 and 511 from a tissue by a nonlinear component of sum frequency component and difference-frequency component generated in the process of propagation of the second transmit pulse 211 in a biological body, and a contrast echo component 611.

By adding the received echo R1 and the received echo R2, the linear tissue echo components 310 and 311 are removed because of the linear process. Finally, the contrast echo component 612 obtained by adding the contrast echo components 610 and 611, a sum frequency tissue harmonic echo component 412 obtained by adding the sum frequency tissue harmonic echo components 410 and 411 and a difference-frequency tissue harmonic echo component 512 obtained by adding the difference-frequency tissue harmonic echo components 510 and 511 are extracted.

According to this pulse inversion technique, intensities of the sum frequency tissue harmonic echo component 412 and the difference-frequency tissue harmonic echo component 512 are smaller than the intensities of the removed linear tissue echo components 310 and 311 for the fundamental wave and a signal component of the contrast echo component 612 widely included in the probe sensitivity band 10 is used to form an image. Therefore, it is possible to construct a vascular image with the contrast echo which is not comparatively buried in a wide band signal from the tissue.

As described above, in the ultrasound contrast imaging, it is important to increase an intensity ratio of the echo from the ultrasound contrast agent and the echo from the body tissue (referred to as a contrast-to-tissue ratio or CTR). Therefore, in addition to the above-mentioned related art, a method of increasing a CTR is disclosed as follows.

For example, in Patent Literature 1, a method that performs a transmit and receive sequence in which an amplitude and a phase are controlled for the same scanning line three times or more at the time of transmission and reception, respectively to suppress a tissue echo component is disclosed. According to the related art, as an example of three transmit and receive sequences, first transmission and reception is performed by a transmit pulse P1 having an amplitude of 1 and a phase of 0 degree, second transmission and reception is performed by a transmit pulse P2 having an amplitude of 2 and a phase of 180 degrees, and third transmission and reception is performed by a transmit pulse P3 having an amplitude of 1 and a phase of 0 degree and the three received echoes are added with a weight of 1:1:1. As a result, a linear component of a tissue echo is suppressed, but an echo from a contrast agent shows a nonlinear response with respect to the amplitude or the phase of the transmit pulse, and thus is not suppressed by the addition. Therefore, the contrast echo and the tissue echo are intended to be separated. The main difference from the related art described with reference to FIGS. 2 and 3 is that the CTR is increased by aggressively using the contrast echo component with respect to the fundamental component of the transmit pulse.

As another example of a method of increasing a CTR, in Patent Literature 2, a method that increases the CTR by transmitting and receiving two times or more a transmit pulse in which a frequency band of a sum frequency tissue harmonic echo component is generated out of a probe sensitivity band on the same scanning line and aggressively using the contrast echo component for the fundamental component of the transmit pulse is disclosed. The two or more transmit pulses are differently modulated in at least one of an amplitude, a phase, and a polarity and the linear tissue echo component and the sum frequency tissue harmonic echo component are suppressed to increase the CTR.

CITATION LIST

Patent Literature

Patent Literature 1: U.S. Pat. No. 6,494,841
Patent Literature 2: Japanese Unexamined Patent Application Publication No. 2004-504911

SUMMARY OF INVENTION

Technical Problem

In the above-mentioned related art, the method of increasing a CTR is largely divided into two methods mainly depending on a frequency component of the contrast echo used for the imaging. One method uses a response in the second harmonic band of the contrast agent as described with reference to FIGS. 2 and 3. The other method uses a response in the fundamental frequency band of the contrast agent as disclosed in Patent Literature 1 and Patent Literature 2.

According to the former method, a sum frequency tissue harmonic echo component is present in a region of the contrast echo component to be used. Further, if a wide band transmit pulse is used, the difference-frequency tissue harmonic echo component is also included in the probe sensitivity band. Therefore, from the viewpoint of the CTR, a T component is larger than a C component.

The latter method mainly uses a response of the fundamental frequency band of the contrast agent. However, in the technology disclosed in Patent Literature 1, the nonlinear tissue echo component is also included in the probe sensitivity band. From the viewpoint of the CTR, the C component is improved to increase the CTR. However, if an acoustic pressure of the transmit pulse is large, a comparatively large amount of T component may be generated.

Further, in the technology disclosed in Patent Literature 2, among the nonlinear tissue echo components, the sum frequency tissue harmonic echo component is generated out of the probe sensitivity band and the difference-frequency tissue harmonic echo component is generated in the probe sensitivity band. If a comparatively wide band transmit pulse having a large acoustic pressure is used, the difference-frequency tissue harmonic echo component is too large to be ignored, which may lower the CTR.

Solution to Problem

The present invention has been made in an effort to provide an ultrasound diagnosis device that visualizes a high CTR ultrasound contrast image by substantially suppressing or excluding both a sum frequency tissue harmonic echo component and a difference-frequency tissue harmonic echo component.

The ultrasound diagnosis device according to the invention transmits a transmit pulse to a subject and receives an echo reflected from an ultrasound contrast agent injected into the subject by an ultrasound probe to form an image. By the acoustic nonlinearity of the subject, in the process of propagation of the transmit pulse in the subject, the transmit pulse is transmitted so as to exclude one or both of the sum frequency component and the difference-frequency component generated by the nonlinear interaction of frequency components of the transmit pulse from the sensitivity frequency band of the ultrasound probe. In this case, the sensitivity frequency band of the probe refers to a frequency band of an ultrasound wave which may be transmitted or received by the probe.

Further, the ultrasound diagnosis device according to the invention that transmits a transmit pulse to a subject and receives an echo reflected from an ultrasound contrast agent injected into the subject by an ultrasound probe to form an image includes a unit that, by the acoustic nonlinearity of the subject, in the process of propagation of the transmit pulse in the subject, transmits the transmit pulse, so as to exclude one or both of the sum frequency component and the difference-frequency component generated by the nonlinear interaction of frequency components of the transmit pulse from frequency band of the transmit pulse and extracts a band component corresponding to the frequency band of the transmit pulse of an echo received by the ultrasound probe.

The contrast echo used to form an image is transmitted and received two times on the same scanning line in order to suppress the tissue echo for the fundamental component mainly using a response for the region of the fundamental component of the transmit pulse like the pulse inversion technique. As for the two times transmission and reception, an amplitude modulation and phase inversion is performed and a transmit-and-receive sequence processing is performed so as to suppress the tissue echo for the fundamental component.

According to a first aspect of the present invention, the following ultrasound diagnosis device is provided. Specifically, a receive echo R on a scanning line is obtained from a first receive echo R1 that transmits and receives a first transmit pulse P1 from an ultrasound probe having a sensitivity frequency band of a center frequency $f_{pc}$ and a fractional bandwidth Bp and a second receive echo $R_2$ that transmits and receives a second transmit pulse P2 from the ultrasound probe on the same scanning line as the first transmit pulse P1. In this case, the first transmit pulse P1 is set as a pulse having a center frequency which is substantially equal to the center frequency $f_{pc}$ and a fractional bandwidth of $(2-B_p)/2$ or less, and the second transmit pulse P2 is set as a pulse obtained by multiplying 1/n (n>0) to an amplitude of the first transmit pulse P1. Further, the receive echo R is obtained by subtracting the first receive echo R1 and a receive echo R2' obtained by multiplying n to the second receive echo R2 so that a received signal in which a tissue echo component is suppressed may be obtained.

According to a second aspect of the present invention, the following ultrasound diagnosis device is provided. Specifically, a receive echo R on a scanning line is obtained from a first receive echo R1 that transmits and receives a first transmit pulse P1 from the ultrasound probe having a sensitivity frequency band of a center frequency $f_{pc}$ and a fractional bandwidth $B_p$ and a second receive echo R2 that transmits and receives a second transmit pulse P2 from the ultrasound probe on the same scanning line as the first transmit pulse P1. In this case, the first transmit pulse P1 is set as a pulse having a center frequency which is substantially equal to the center frequency and a fractional bandwidth of $(2-B_p)/2$ or less, and the second transmit pulse P2 is set as a pulse obtained by multiplying 1/n (n>0) to an amplitude of the first transmit pulse P1 and having an inversion phase. Further, the receive echo R is obtained by adding the first receive echo R1 and a receive echo R2' obtained by multiplying n to the second receive echo R2 so that a received signal in which a tissue echo component is suppressed may be obtained.

According to a third aspect of the present invention, the following ultrasound diagnosis device is provided. Specifically, a receive echo R on a scanning line is obtained from a first receive echo R1 that transmits and receives a first transmit pulse P1 from an ultrasound probe having a sensitivity frequency band of a fractional bandwidth of ⅔ or higher and a second receive echo R2 that transmits and receives a second transmit pulse P2 from the ultrasound probe on the same scanning line as the first transmit pulse P1. In this case, the first transmit pulse P1 is set as a pulse having a frequency band of a fractional bandwidth of ⅔ or lower, and the second transmit pulse P2 is set as a pulse obtained by multiplying 1/n (n>0) to an amplitude of the first ultrasound pulse P1. Further, a receive echo which is obtained by subtracting the first receive echo R1 and a receive echo R2' obtained by multiplying n to the second receive echo R2 passes a band limiting filter having a frequency band which is substantially equal to the first or second transmit pulse P1 or P2 to obtain a receive echo R. Therefore, it is possible to obtain a received signal in which a tissue echo component is suppressed.

According to a fourth aspect of the invention, the following ultrasound device is provided. Specifically, a receive echo R on a scanning line is obtained from a first receive echo R1 that transmits and receives a first transmit pulse P1 from an ultrasound probe having a frequency sensitivity band having a ⅔ or higher fractional band and a second receive echo R2 that transmits and receives a second transmit pulse P2 on the same scanning line as the first transmit pulse P1 from the ultrasound probe. In this case, the first transmit pulse P1 is a pulse having a frequency band whose fractional bandwidth is ⅔ or lower and the second transmit pulse P2 is set to a pulse having an amplitude obtained by multiplying 1/n to an amplitude of the first transmit pulse P1 and phase inversion. Further, the receive echo obtained by adding the first receive echo R1 and a receive echo R2' obtained by multiplying n to the second receive echo R2 passes a band limiting filter having a frequency band which is substantially equal to the first or second transmit pulse P1 or P2 to obtain a receive echo R so that a received signal in which a tissue echo component is suppressed may be obtained.

According to a fifth aspect of the present invention, the following ultrasound diagnosis device is provided. Specifically, in the third and fourth aspects, a lower limit frequency of the sensitivity frequency band of the ultrasound probe may be substantially equal to a lower limit frequency of the frequency band of the first transmit pulse P1. Therefore, it is possible to improve a sensitivity of a contrast echo in a deep part of the subject.

According to a sixth aspect of the present invention, the following ultrasound diagnosis device is provided. Specifically, in the third and fourth aspects, an upper limit frequency of the sensitivity frequency band of the ultrasound probe may be substantially equal to an upper limit frequency of the frequency band of the first transmit pulse P1. Therefore, it is possible to obtain a high resolution contrast image.

n which indicates a ratio of an amplitude of the first ultrasound pulse P1 and an amplitude of the second ultrasound pulse P2 is represented by m-th power of 2 when m is an integer. By doing this, it is possible to reduce a calculation cost.

Further, the n may be set to 2 (the m is 1). By doing this, it is possible to efficiently suppress the tissue echo and extract the contrast echo.

The ultrasound diagnosis device according to the invention may include a receiving unit that receives an instruction from a user to correct or adjust at least one parameters of the amplitude, the center frequency, and the fractional bandwidth of the transmit pulse P1, the amplitude, the center frequency, and the fractional bandwidth of the transmit pulse P2, the amplitude and the phase of the receive echo R1, the amplitude and the phase of the receive echo R2, and n or m parameters. In this case, the ultrasound diagnosis device may include a correcting unit or an adjusting unit that increases or decreases a corresponding parameter depending on the increased or decreased amount of the parameter received by the receiving unit. In the meantime, the ultrasound probe has an array structure including a plurality of channels and the correcting unit or the adjusting unit may be provided for every channel.

An ultrasound diagnosis device may include: a transmitter that includes a waveform generator and an amplifier and generates a transmit signal; an ultrasound probe that converts the transmit signal generated from the transmitter into an acoustic signal to transmit an ultrasound transmit pulse to a subject and receive a reflected echo from the subject; and a receiver that performs a signal processing of the received reflected echo. The ultrasound probe receives a first receive echo R1 that transmits and receives a first transmit pulse P1 which is a pulse having a sensitivity frequency band having ⅔ or higher of a fractional bandwidth and a frequency band having ⅔ or lower of a fractional bandwidth and a second receive echo R2 that transmits and receives a second transmit pulse P2 which is a pulse having an amplitude which is 1/n (n>0) of the amplitude of the first ultrasound pulse P1 on the same scanning line as the first transmit pulse P1 and the receiver includes a signal processor that passes the receive echo obtained by subtracting the first receive echo R1 and a receive echo R2' obtained by multiplying n to the second receive echo R2 through a band limiting filter having a substantially same frequency band as the first or second transmit pulse P1 or P2 to obtain a receive echo R.

An ultrasound diagnosis device may include: a transmitter that includes a waveform generator and an amplifier and generates a transmit signal; an ultrasound probe that converts the transmit signal generated from the transmitter into an acoustic signal to transmit an ultrasound transmit pulse to a subject and receive a reflected echo from the subject; and a receiver that performs a signal processing of the received reflected echo. The ultrasound probe receives a first received echo R1 that transmits and receives a first transmit pulse P1 which is a pulse having a sensitivity frequency band having ⅔ or higher of a fractional bandwidth and a frequency band having ⅔ or lower of a fractional bandwidth and a second receive echo R2 that transmits and receives a second transmit pulse P2 which is a pulse having an amplitude of 1/n (n>0) of the amplitude of the first ultrasound pulse P1 on the same scanning line as the first transmit pulse P1 and inversion phase and the receiver includes a signal processor that passes the receive echo obtained by adding the first receive echo R1 and a receive echo R2' obtained by multiplying n to the second receive echo R2 through a band limiting filter having a substantially same frequency band as the first or second transmit pulse P1 or P2 to obtain a receive echo R.

Advantageous Effect of Invention

According to the aspects of the present invention, a transmitting signal is generated so as not to receive a sum frequency component or a difference-frequency component from an ultrasound probe so that the imaging is achieved using a receiving signal in which a tissue echo component for the fundamental component and a nonlinear tissue echo component for a sum frequency tissue harmonic echo component and a difference-frequency tissue harmonic echo component which are noise components in the ultrasound contrast image are almost removed. Therefore, it is possible to achieve a high CTR and obtain a high quality ultrasound contrast image.

BRIEF DESCRIPTION OF DRAWINGS

FIG. 9 is a frequency spectrum illustrating a relationship of a transmit and receive pulse band and an ultrasound probe sensitivity range at the time of ultrasound contrasting of the ultrasound diagnosis device according to a sixth aspect of the invention.

DESCRIPTION OF EMBODIMENTS

Hereinafter, embodiments of the invention will be described in detail with reference to the drawings.

An embodiment relates to an ultrasound diagnosis device that transmits a transmit pulse to a subject and receives a reflected echo from an ultrasound contrast agent injected into the subject by an ultrasound probe to form an image. The device has a configuration that efficiently excludes a linear tissue echo component for a fundamental component of the transmit pulse and a sum frequency component and a difference-frequency component generated by the nonlinear interaction between frequency components of the transmit pulse during the process of propagating the transmit pulse in the subject due to the acoustic nonlinearity of the subject, that is, a nonlinear tissue echo component. By doing this, it is possible to significantly improve an intensity ratio of an echo from the ultrasound contrast agent and an echo from a body tissue (referred to as contrast-to-tissue ratio or CTR) which is an important index indicating an image quality of an ultrasound contrast image.

Figure 1:
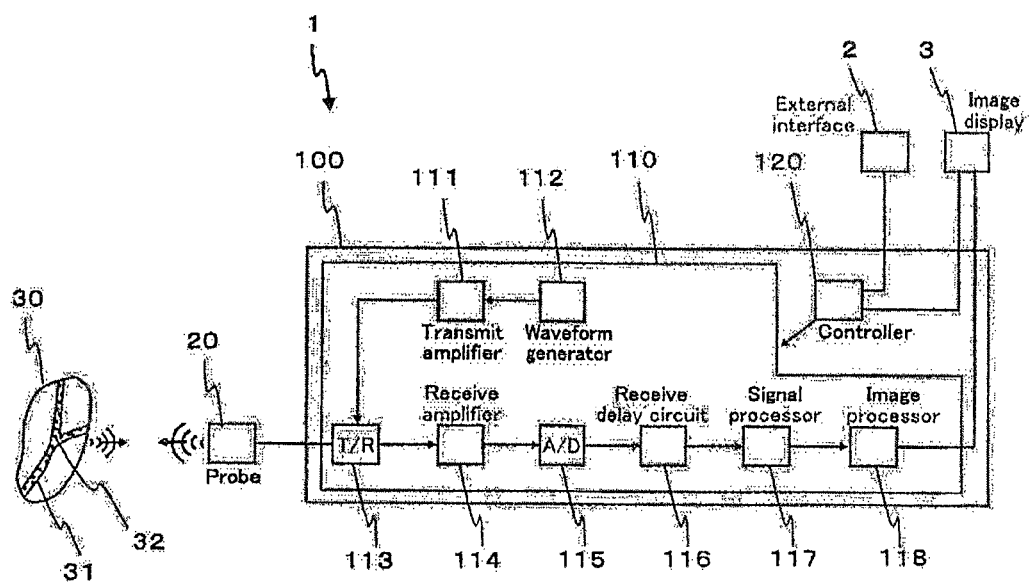
FIG. 1 is a block diagram of a device configuration illustrating an embodiment of an ultrasound diagnosis device of the present invention.
Figure 2:
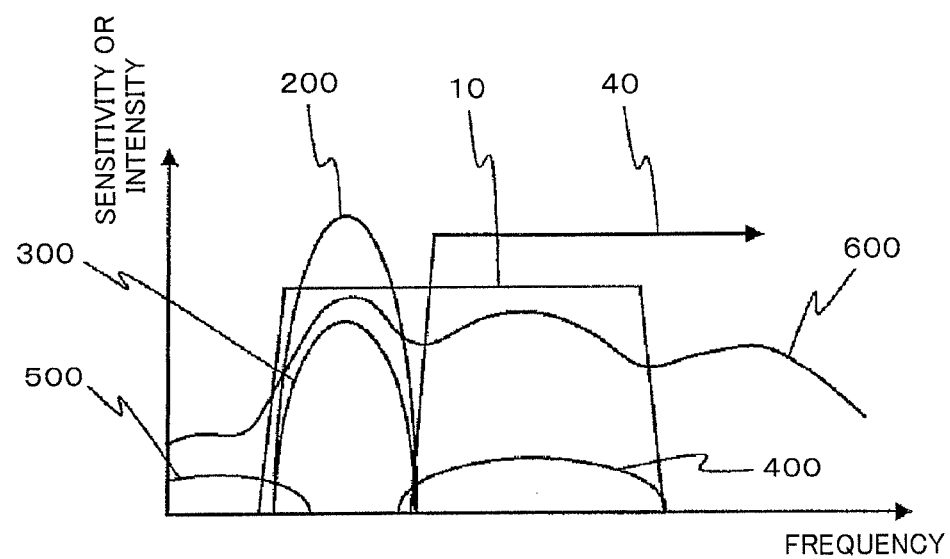
FIG. 2 is a frequency spectrum illustrating a relationship of a transmit and receive pulse band and an ultrasound probe sensitivity band at the time of ultrasound contrasting of an ultrasound diagnosis device of the related art.

First, referring to FIG. 1, an ultrasound diagnosis device according to an embodiment will be described.

The ultrasound diagnosis device 1 includes a probe 20, a main body 100 of the device, an external interface 2, and an image display 3.

The probe 20 converts a transmit signal from the main body 100 into a transmit acoustic signal at the time of transmission and then transmits an ultrasound wave to a subject 30. Thereafter, the probe 20 converts a reflected echo signal from the subject 30 into a received electric signal and transmits the signal to the main body 100. In a blood vessel 31 inside the subject 30, an ultrasound contrast agent 32 is intravenously injected in advance. The probe 20 generally has a one or two dimensional array structure and may focus or steer a transmit beam and a receive beam.

The main body 100 includes a waveform generator 112 that generates a transmit waveform transmitted from the probe 20, a transmit amplifier 111 that amplifies the transmit waveform from the waveform generator 112, a receive amplifier 114 that amplifies a received signal from the probe 20, a transmit and receive (T/R) switch 113 that electrically connects the transmit amplifier 111 and the probe 20 at the time of transmission and electrically connects the receive amplifier 114 and the probe 20 at the time of reception, an A/D converter 115 that converts an analog signal amplified by the receive amplifier 114 into a digital signal, a receive delay circuit 116 that applies a predetermined time delay to the received signal to form a receiving beam, a signal processor 117 that performs a signal processing which will be described in detail below on the receiving beam, an image processor 118 that constructs image data from an output from the signal processor 117, and a controller 120 that controls a transmit and receive timing, the transmit waveform, a receive amplifier gain, the time delay, and the signal processing for the above-mentioned components 110 of the main body.

The output from the image processor 118 is displayed as a video image such as a two dimensional tomographic image or a three dimensional image on the image display 3. An operator allows the controller 120 to control the components on the main body 100 or the image display 3 using the external interface 2. Further, even though the external interface 2 is not provided, the imaging may be performed under a predetermined control condition.

Next, a transmitting and receiving operation of a pulse and a processing sequence in the signal processor 117 in the ultrasound diagnosis device according to the invention will be described with reference to FIGS. 5 and 6.

Figure 5:
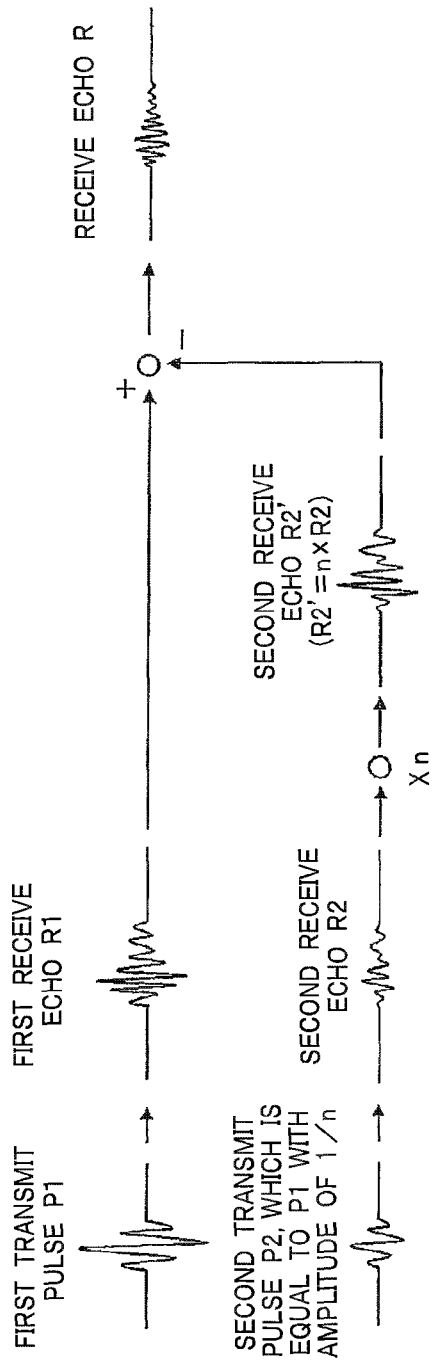
FIG. 5 is a signal processing flowchart illustrating a transmit and receive sequence at the time of ultrasound contrasting of the ultrasound diagnosis device according to the first aspect of the invention.
Figure 6:
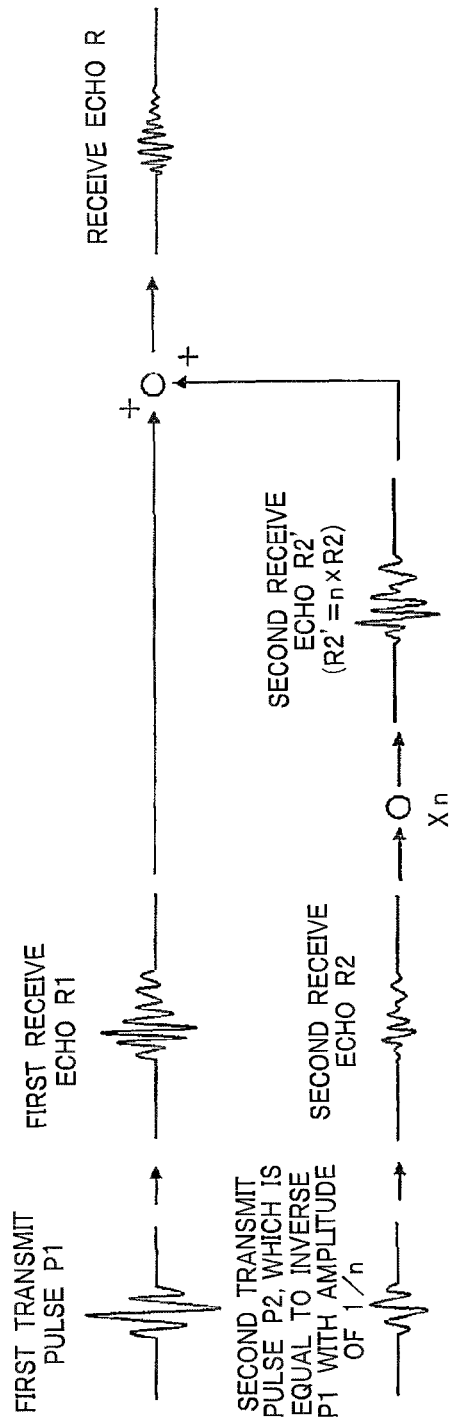
FIG. 6 is a signal processing flowchart illustrating a transmit and receive sequence at the time of ultrasound contrasting of the ultrasound diagnosis device according to the second aspect of the invention.

In the ultrasound diagnosis device of the present invention, as illustrated in FIGS. 5 and 6, one receive data is obtained by transmission and reception at least two pulse sequences. FIG. 5 illustrates a transmit and receive sequence at the time of ultrasound contrasting of the ultrasound diagnosis device according to a first aspect of the invention and FIG. 6 illustrates a transmit and receive sequence at the time of ultrasound contrast imaging of the ultrasound diagnosis device according to a second aspect of the invention. Further, a frequency band of a transmit pulse which is a feature of the invention will be described in detail below.

First, in the waveform generator 112, a predetermined transmit pulse waveform is formed by the controller 120 and a first transmit pulse P1 is irradiated onto the subject 30 from the probe 20 through the transmit amplifier 111 and the transmit and receive switch 113. The first transmit pulse P1 causes a waveform distortion by a nonlinear acoustic effect of a tissue inside the subject 30 and is propagated in portions having different acoustic impedances while repeating the reflection and the transmission. Further, due to the presence of the ultrasound contrast agent 32 inside the blood vessel 31, the first transmit pulse P1 is reflected or scattered by the ultrasound contrast agent 32. Further, in the ultrasound contrast agent 32, nonlinear vibration is excited by the first transmit pulse P1.

If the first transmit pulse P1 is irradiated from the probe 20, the transmit and receive switch 113 electrically connects the receive amplifier 114 and the probe 20 in accordance with the instruction from the controller 120. An echo reflected from the subject 30 continuously reaches the probe 20 as a first received echo R1 in the order of positions closer to the probe 20 and the transmission and reception of a first pulse sequence is completed after a time when the first receive echo R1 is considered to return from the deepest portion of a capturing area elapses. The first receive echo R1 is transmitted to the signal processor 117 through the transmit and receive switch 113, the receive amplifier 114, the A/D converter 115, and the receive delay circuit 116 and temporarily stored in a temporary memory provided in the signal processor 117 which is not illustrated.

After completing transmission and reception of the first pulse sequence, the transmit amplifier 111 and the probe 20 are electrically connected again by the transmit and receive switch 113. Next, the waveform generator 112 forms another transmit pulse waveform and transmits the transmit pulse waveform to the probe 20 through the transmit amplifier 111 and the transmit and receive switch 113 and a second transmit pulse P2 is irradiated onto the subject 30 from the probe 20.

In the ultrasound diagnosis device according to the first aspect of the present invention, as illustrated in FIG. 5, the second transmit pulse P2 is a waveform which has a size equal to 1/n (n>0) of an amplitude of a waveform of the first transmit pulse P1. Further, in the ultrasound diagnosis device according to the second aspect of the present invention, as illustrated in FIG. 6, the second transmit pulse P2 is a waveform which is obtained by substantial inversion phase of the waveform of the first transmit pulse P1 and has a size equal to 1/n (n>0) of the amplitude of a waveform of the first transmit pulse P1. The waveform generator 112, for example, may include a unit that removes electrical distortion generated in the transmit amplifier 111 or influence of a phase rotation depending on the frequency characteristic of the probe 20 and adjusts at least one of the first transmit pulse P1 and the second transmit pulse P2.

The second transmit pulse P2 is propagated in portions having different specific acoustic impedances by repeating reflection and the transmission while generating a waveform distortion by a nonlinear acoustic effect of a tissue inside the subject 30. Further, due to the presence of the ultrasound contrast agent 32 inside the blood vessel 31, the second transmit pulse P2 is reflected or scattered by the ultrasound contrast agent 32. Further, in the ultrasound contrast agent 32, nonlinear vibration is excited by the second transmit pulse P2.

If the second transmit pulse P2 is transmitted from the probe 20, the transmit and receive switch 113 electrically connects the receive amplifier 114 and the probe 20 in accordance with the instruction from the controller 120. The echo reflected from the subject 30 continuously reaches the probe 20 as a second received echo R2 in the order of positions closer to the probe 20 and the transmission and reception of a second pulse sequence is completed after a time when the second receive echo R2 is considered to return from the deepest portion of a capturing area elapses. The second receive echo R2 is transmitted to the signal processor 117 through the transmit and receive switch 113, the receive amplifier 114, the A/D converter 115, and the receive delay circuit 116 and temporarily stored in a temporary memory provided in the signal processor 117 which is not illustrated.

In the signal processor 117, the following signal processing is performed using the first receive echo R1 and the second receive echo R2 stored in the temporary memory. Specifically, in the ultrasound diagnosis device according to the first aspect of the present invention, as illustrated in FIG. 5, a receive echo R is obtained by subtraction of the first receive echo R1 and a second receive echo R2' obtained by multiplying n to the second receive echo R2. Further, in the ultrasound diagnosis device according to the second aspect of the present invention, as illustrated in FIG. 6, the receive echo R is obtained by addition of the first receive echo R1 and a second receive echo R2' obtained by multiplying n to the second receive echo R2.

The above-mentioned first receive echo R1 is a reflected echo of the first transmit pulse P1 from the subject 30 and the reflected echo component is formed of a linear tissue echo component of the first transmit pulse P1 from a body tissue or blood vessel that forms the subject 30, a nonlinear tissue echo component generated during the process of propagating the first transmit pulse P1 in the subject 30, and a contrast echo component generated by nonlinear vibration of the ultrasound contrast agent 32 excited by the first transmit pulse P1 or reflection and scattering of the first transmit pulse P1 by the ultrasound contrast agent 32. The second receive echo R2 is a reflected echo of the second transmit pulse P2 from the subject 30. The reflected echo component is formed of a linear tissue echo component of the second transmit pulse P2 from a body tissue or blood vessel that forms the subject 30, a nonlinear tissue echo component generated during the process of propagating the second transmit pulse P2 in the subject, and a contrast echo component generated by nonlinear vibration of the ultrasound contrast agent 32 excited by the second transmit pulse P2 or reflection and scattering of the second transmit pulse P2 by the ultrasound contrast agent 32. Among these, the linear tissue echo component exhibits linear behavior caused by inversion of the waveform or n times of the waveform amplitude. Therefore, by the processing sequence illustrated in FIG. 5 or 6, the linear tissue echo component is removed from the receive echo R.

In the meantime, if n is m-th power of 2 (m is an integer), digital processing of the multiplication of n may be performed by a bit shift, which lowers an operation cost and improves the processing speed. Further, n is multiplied to the second receive echo R2 in order to remove the linear tissue echo component by subtraction or addition of the first receive echo R1 and the second receive echo R2'. Since n is multiplied to the second receive echo R2 after passing through the A/D converter 115, n which is multiplied to the second receive echo R2 may be optimally adjusted so as to fully remove the linear tissue echo component including a quantization error.

Figure 4:
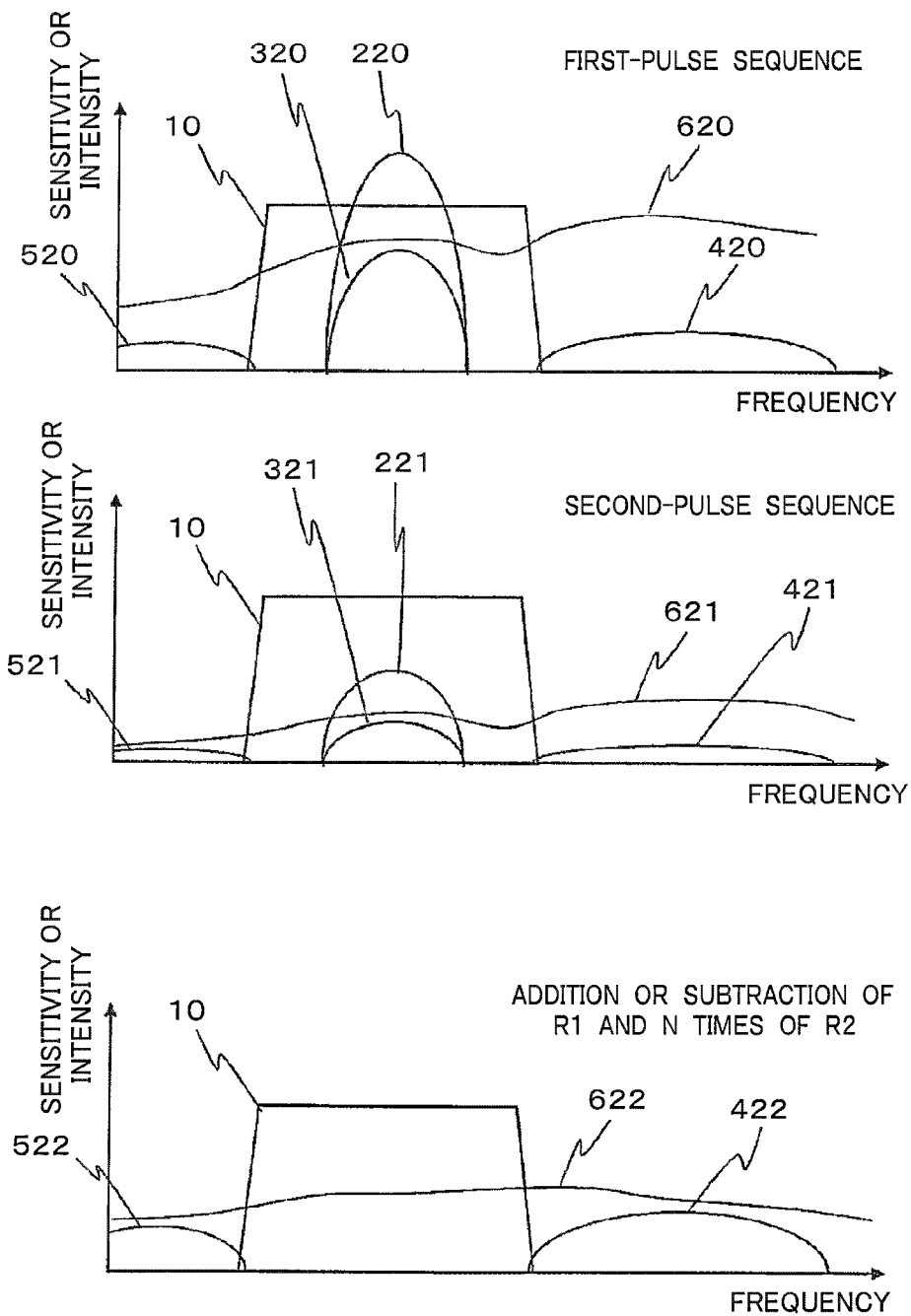
FIG. 4 is a frequency spectrum illustrating a relationship of a transmit and receive pulse band and an ultrasound probe sensitivity band at the time of ultrasound contrasting of an ultrasound diagnosis device according to first and second aspects of the invention.

Next, a frequency band of the first transmit pulse P1 and the second transmit pulse P2 which are the feature of the present invention will be described in detail with reference to FIG. 4.

This embodiment has frequency bands of the frequency component 220 and the frequency component 221 as fundamental components of the first transmit pulse P1 at the first pulse sequence and the second transmit pulse P2 at the second pulse sequence, respectively. A frequency component of the receive echo of the first transmit pulse P1 immediately before being received by the probe 20 is configured by a linear tissue echo component 320 for the fundamental component, a sum frequency tissue harmonic echo component 420 generated by nonlinear interaction of the frequency components 220 in the subject 30 that form the first transmit pulse P1, a difference-frequency tissue harmonic echo component 520 generated by nonlinear interaction of the frequency components 220 in the subject 30 that form the first transmit pulse P1, and a contrast echo component 620 generated by nonlinear vibration of the ultrasound contrast agent 32 excited by the first transmit pulse P1 or reflection and scattering of the first transmit pulse P1 by the ultrasound contrast agent 32. Further, a frequency component of the receive echo of the second transmit pulse P2 immediately before being received by the probe 20 is configured by a linear tissue echo component 321 for the fundamental component, a sum frequency tissue harmonic echo component 421 generated by nonlinear interaction of the frequency components 221 in the subject 30 that form the second transmit pulse P2, a difference-frequency tissue harmonic echo component 521 generated by nonlinear interaction of the frequency components 221 in the subject 30 that form the second transmit pulse P2, and a contrast echo component 621 generated by nonlinear vibration of the ultrasound contrast agent 32 excited by the second transmit pulse P2 or reflection and scattering of the second transmit pulse P2 by the ultrasound contrast agent 32.

In order to obtain a high CTR ultrasound contrast image, it is considered to efficiently capture the contrast echo components 620 and 621 and efficiently suppress or exclude the linear tissue echo components 220 and 221 or nonlinear tissue echo components 420, 520, 421, and 521. The best feature of the present invention is to suppress the nonlinear tissue echo components 420, 520, 421, and 521, which cannot be removed using a linear operation such as the pulse inversion technique, by the probe sensitivity band 10 of the probe 20. Specifically, the first transmit pulse P1 and the second transmit pulse P2 are transmitted so as to exclude the sum frequency tissue harmonic echo components 420 and 421 from the high frequency band of the probe sensitivity band 10 and remove the predetermined difference-frequency tissue harmonic echo components 520 and 521 out of the low frequency band of the probe sensitivity band 10.

The linear tissue echoes 320 and 321 for the fundamental components of the first transmit pulse P1 and the second transmit pulse P2 show a linear behavior caused by the inversion of the waveform or the n times of the amplitude of the waveform. Therefore, as described above, the linear tissue echoes 320 and 321 may be removed by the linear operation of the first receive echo R1 and the second receive echo R2. In contrast, the sum frequency tissue harmonic echo components 420 and 421 or the difference-frequency tissue harmonic echo components 520 or 521 are not removed by the multiplication of n, subtraction, or addition. If there is no band limitation by the probe sensitivity band 10 of the probe 20, the sum frequency tissue harmonic echo components 420 and 421 or the difference-frequency tissue harmonic echo components 520 or 521 may remain even when using the subtraction or addition of the first receive echo R1 and n times of the second receive echo R2 as a sum frequency tissue harmonic echo component 422 and a difference-frequency tissue harmonic echo component 522. However, in the present invention, the first transmit pulse P1 and the second transmit pulse P2 are formed so as to exclude any of the sum frequency tissue harmonic echo components and the difference-frequency tissue harmonic echo components out of the frequency band of the probe sensitivity band 10. Therefore, these nonlinear tissue echo components are removed by being received by the probe 20.

As described above, in addition to the band limitation in the probe sensitivity band 10, in order to suppress the nonlinear tissue echo component, the relationship of the amplitudes or the phases of the first transmit pulse P1 and the second transmit pulse P2 may be set to be further equal to each other. The nonlinear tissue echo is represented by the waveform distortion accompanied with the nonlinear acoustic propagation in the tissue in the subject 30 and the sum frequency component and the difference-frequency component are generated based on the phase relationship of the fundamental transmit pulse. For example, a second harmonic component which is represented as the sum frequency component is generated with the same phase as the fundamental transmit pulse and the waveform distortion is accumulated during the propagation. The distortion amount of the waveform distortion specifically depends on an acoustic pressure. Therefore, an energy conversion to a nonlinear component is significant as the acoustic pressure is increased so that an amount of the waveform distortion is increased. Therefore, in the first transmit pulse P1 and the second transmit pulse P2, the phases or amplitudes of the nonlinear tissue echoes to be generated become equal to each other as the phases are equal and a ratio n of the amplitudes of both pulses is close to 1. In this case, since the phases of the first transmit pulse P1 and the second transmit pulse P2 become equal to each other by the subtraction of the first receive echo R1 and the second receive echo R2', the processing sequence after reception performs the subtraction illustrated in FIG. 5. By the transmit and receive sequence, the nonlinear tissue echo is suppressed by the subtraction after reception in addition to the probe sensitivity band 10 so as to increase the CTR.

Further, as described above, in order to reduce the operation cost or improve the processing speed, n may be m-th power of 2 (m is an integer). With this consideration, as n which is closest to 1, n=2 may be used. Specifically, if an amplitude of the first transmit pulse P1 is $P_0$, an amplitude of the second transmit pulse P2 may be $P_0/2$. The probe 20, which is generally used for the ultrasound diagnosis device, has an array structure in which electro-acoustic conversion elements such as piezoelectric elements are arranged in a plurality of channels. Therefore, ultrasound beam is focused in a desired scanning direction at the time of transmission and reception to improve an S/N ratio of a transmit and receive signal. In this case, the condition that the amplitude of the first transmit pulse P1 is $P_0$ and the amplitude of the second transmit pulse P2 is $P_0/2$ is satisfied when a ratio of the amplitudes of the acoustic pressure to the ultrasound beam by the transmit focused first transmit pulse P1 and the ultrasound beam by the second transmit pulse P2 is 2. A method that forms the first transmit pulse P1 and the second transmit pulse P2 from the probe 20 with this array structure will be described with reference to FIGS. 10 and 11.

Figure 10:
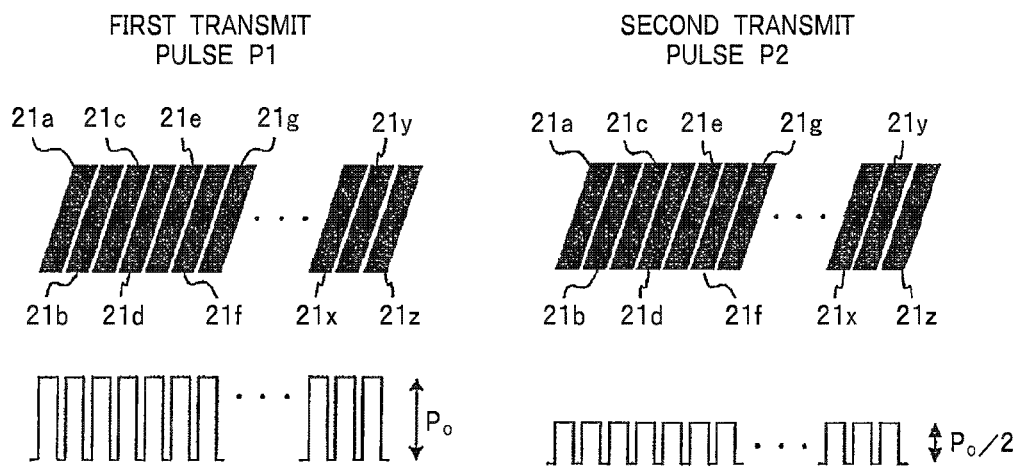
FIG. 10 is a schematic view illustrating an array aperture amplitude apodization when the ultrasound diagnosis device according to the invention transmits an ultrasound wave.

FIG. 10 is a schematic view illustrating an array aperture amplitude apodization when the ultrasound diagnosis device according to the invention transmits an ultrasound wave. In the probe 20, electro-acoustic conversion elements 21a to 21z such as piezoelectric elements are, for example, one-dimensionally arranged as illustrated in FIG. 10. The waveform generator 112 has a function that selectively changes an applied voltage or delay time of each channel of the electro-acoustic conversion elements 21a to 21z and an applied voltage is applied to each channel through the transmit amplifier 111 and the transmit and receive switch 113. As illustrated in FIG. 10, first, at the first pulse sequence, the first transmit pulse P1 having a sound pressure amplitude $P_0$ is transmitted from the electro-acoustic conversion elements 21a to 21z used to focus the transmit beam. Next, at the second pulse sequence, the second transmit pulse P2 having a sound pressure amplitude $P_0/2$ is transmitted from the electro-acoustic conversion elements 21a to 21z used to focus the transmit beam. By these transmit sequences, the amplitude ratio of the sound pressure to the ultrasound beam by the first transmit pulse P1 and the ultrasound beam by the second transmit pulse P2 may be 2. Further, the waveform generator 112 may include a unit that corrects or adjusts an irregularity of the transmit sensitivity of the electro-acoustic conversion elements 21a to 21z or a pulse shape (center frequency or fractional bandwidth of the transmit pulse). Further, as a result of the subtraction of the first receive echo R1 and the second receive echo R2', the linear tissue echo may be corrected or adjusted so as to be mostly suppressed. The sensitivity, the center frequency, or the fractional bandwidth may be corrected or adjusted at a level of the first receive echo R1 or the second receive echo R2. For example, the receive delay circuit 116 that forms the receive beam may have a correcting or adjusting function.

Figure 11:
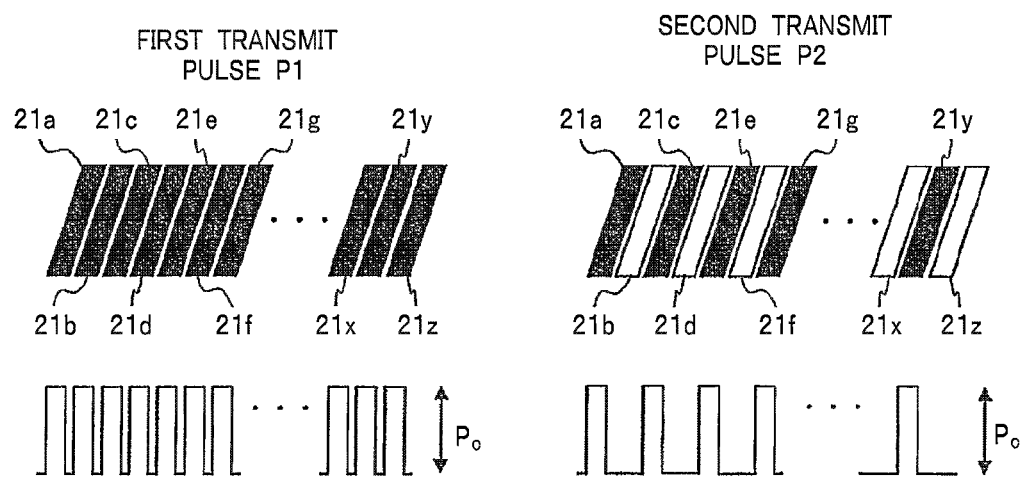
FIG. 11 is a schematic view illustrating another array aperture amplitude apodization when the ultrasound diagnosis device according to the invention transmits an ultrasound wave.

FIG. 11 is a schematic view illustrating another array aperture amplitude apodization when the ultrasound diagnosis device according to the invention transmits an ultrasound wave. In FIG. 11, in order to set the amplitude ratio of the sound pressure to the ultrasound beam by the first transmit pulse P1 and the ultrasound beam by the second transmit pulse P2 to be 2, the transmit areas at the first pulse sequence and the second pulse sequence are changed. Specifically, the first transmit pulse P1 at the first pulse sequence is transmitted from all electro-acoustic conversion elements 21a to 21z with a sound pressure amplitude $P_0$ and the second transmit pulse P2 at the second pulse sequence is transmitted such that the sound pressure amplitude for every channel is repeated between $P_0$ and 0. By such a transmit sequence, a transmit area of the ultrasound beam by the second transmit pulse P2 is half the transmit area at the first pulse sequence. Therefore, the amplitude ratio of the transmit sound pressure may be 2 at a level of the ultrasound beam. Also in this case, the waveform generator 112 has a function that selectively changes an applied voltage or delay time of each channel of the electro-acoustic conversion elements 21a to 21z and may have a configuration in which an applied voltage is applied to each channel through the transmit amplifier 111 and the transmit and receive switch 113. By this transmit sequence, the same conditional voltage is applied to the electro-acoustic conversion element which transmits a sound wave at the first pulse sequence and the second pulse sequence so that the influence of the voltage dependent waveform distortion on the electro-acoustic conversion elements 21a to 21z or the transmit amplifier 111 may be removed. Further, the waveform generator 112 may include a unit that corrects an irregularity of a transmit and receive sensitivity of the electro-acoustic conversion elements 21a to 21z. As a result of the subtraction of the first receive echo R1 and the second receive echo R2', the irregularity of the transmit and receive sensitivity may be corrected so as to mostly suppress the linear tissue echo. The sensitivity, the center frequency, or the fractional bandwidth may be corrected or adjusted at a level of the first receive echo R1 or the second receive echo R2. For example, the receive delay circuit 116 that forms the receive beam may have a correcting or adjusting function.

In the meantime, the ultrasound contrast agent 32 has a configuration similar to a microcapsule that includes a cavity therein and shows a nonlinear response (expansion and contraction) with respect to the ultrasound excitation from the surroundings. The nonlinearity means that the sound pressure or the phase of the surrounding ultrasound wave is nonlinear. The contrast echo components 620 and 621 for the first transmit pulse P1 and the second transmit pulse P2 basically have different amplitude or phase relationship. Further, even though the first transmit pulse P1 and the second transmit pulse P2 are perfectly same transmit pulse, the transmit and receive timings are temporally deviated at the first pulse sequence and the second pulse sequence. Therefore, aggregative shapes of the ultrasound contrast agent 32 may be varied at the time of transmitting and receiving the first transmit pulse P1 and at the time of transmitting and receiving the second transmit pulse P2. Therefore, the contrast echo component by the reflected wave or scattered wave from the aggregate of the ultrasound contrast agent 32 may be also varied at the time of transmitting and receiving the first transmit pulse P1 and at the time of transmitting and receiving the second transmit pulse P2. Accordingly, even though the contrast echo component 620 and n times of the contrast echo component 621 are subtracted or added, the contrast echo component 622 remains as a signal. Therefore, even though a band is limited by the probe sensitivity band 10, specifically the response for the fundamental component of the transmit pulse is captured as a main contrast echo component.

As described above, according to the ultrasound diagnosis device of the present invention, a contrast signal is obtained from the contrast echo component 622 through the probe sensitivity band 10 and the linear tissue echo component for the fundamental wave is suppressed by the linear operation processing of the linear tissue echo component 320 obtained at the first pulse sequence and the linear tissue echo component 321 obtained at the second pulse sequence and is removed by the band limitation by the probe sensitivity band 10 mainly using the difference or sum frequency tissue harmonic echo component. Therefore, it is possible to obtain a high CTR ultrasound contrast image.

Next, a transmit pulse condition that generates the sum frequency tissue harmonic echo components 420 and 421 and the difference-frequency tissue harmonic echo components 520 and 521 out of the frequency band of the probe sensitivity band 10 will be described in detail.

First, it is assumed that the frequency band of the probe sensitivity band 10 is $f_{p1}$ to $f_{p2}$ and the frequency band of the first transmit pulse P1 or the second transmit pulse P2 is $f_{t1}$ to $f_{t2}$. Here, the frequency band is generally defined as −6 dB bandwidth. However, in the present invention, the frequency band is a frequency bandwidth having sensitivity or intensity which may affect the final ultrasound contrast image but is not limited to −6 dB bandwidth.

The frequency band of a transmit sum frequency component generated by the nonlinear acoustic propagation of the first transmit pulse P1 or the second transmit pulse P2 whose frequency band is $f_{t1}$ to $f_{t2}$ is determined as a sum frequency component of all frequency components which forms the first transmit pulse P1 or the second transmit pulse P2 to be $2f_{t1}$ to $2f_{t2}$. Further, the frequency band of a transmit difference-frequency component generated by the nonlinear acoustic propagation of the first transmit pulse P1 or the second transmit pulse P2 whose frequency band is $f_{t1}$ to $f_{t2}$ is determined as a difference-frequency component of all frequency components which forms the first transmit pulse P1 or the second transmit pulse P2 to be DC to $f_{t2}-f_{t1}$. The sum and difference frequency tissue harmonic echo components 420 and 520 for the first transmit pulse P1 or the sum and difference frequency tissue harmonic echo components 421 and 521 for the second transmit pulse P2 are the reflected echo components for the transmit sum frequency component and the transmit difference-frequency component. Therefore, the frequency bands of the sum frequency tissue harmonic echo components 420 and 421 are $2f_{t1}$ to $2f_{t2}$ and the frequency bands of the difference-frequency tissue harmonic echo components 520 and 521 are DC to $f_{t2}-f_{t1}$. Therefore, a condition that generates the sum frequency tissue harmonic echo components 420 and 421 and the difference-frequency tissue harmonic echo components 520 and 521 out of the frequency band of the probe sensitivity band 10 is as follows:

$$f_{p1} \ge f_{t2}-f_{t1}, f_{p2} \le 2f_{t1}$$

Therefore, as a condition that obtains a high resolution image, in order to obtain the first transmit pulse P1 or the second transmit pulse P2 having a maximum frequency band, the frequency band of the first transmit pulse P1 or the second transmit pulse P2 becomes $f_{p2}/2$ to $f_{p1}+f_{p2}/2$.

Here, if the frequency band condition $f_{p1}$ to $f_{p2}$ of the probe sensitivity band 10 is represented by the center frequency and the fractional bandwidth and the center frequency is $f_{pc}$ and the fractional bandwidth is $B_p$, the following relational expressions are established.

$$f_{p1}=((2-B_p)/2)f_{pc}$$

$$f_{p2}=((2+B_p)/2)f_{pc}$$

If the frequency band condition $f_{p2}/2$ to $f_{p1}+f_{p2}/2$ of the first transmit pulse P1 or the second transmit pulse P2 is rewritten using these relational expressions, $$(f_{p2}/2 \text{ to } f_{p1}+f_{p2}/2) \rightarrow ((2+B_p)f_{pc}/4 \text{ to } (6-B_p)f_{pc}/4).$$

Further, if the frequency band condition $f_{t1}$ to $f_{t2}$ of the first transmit pulse P1 or the second transmit pulse P2 is rewritten with the center frequency $f_{tc}$ ($=(f_{t1}+f_{t2})/2$) and the fractional bandwidth $B_t$ ($=(f_{t2}-f_{t1})/f_{tc}$), the following relational expression for the center frequency $f_{tc}$ is obtained:

$$f_{tc} = (f_{t1} + f_{t2})/2$$
$$= ((2 + B_p)f_{pc}/4 + (6 - B_p)f_{pc}/4)/2$$
$$= f_{pc}$$

In other words, the center frequency $f_{tc}$ of the first transmit pulse P1 or the second transmit pulse P2 becomes to be equal to the center frequency of the probe sensitivity band 10. Next, the following relational expression for the fractional bandwidth $B_t$ is obtained:

$$B_t = (f_{t2} - f_{t1})/f_{tc}$$
$$= ((6 - B_p)f_{pc}/4 - (2 + B_p)f_{pc}/4)/f_{pc}$$
$$= (2 - B_p)/2$$

From the above expressions, for example, if the fractional bandwidth $B_p$ of the probe 20 is 80%, the fractional bandwidth of the first transmit pulse P1 and the second transmit pulse P2 becomes 60%. Further, if the fractional bandwidth $B_p$ of the probe 20 is 100%, the fractional bandwidths of the first transmit pulse P1 and the second transmit pulse P2 become 50%. Generally, since the fractional bandwidth $B_p$ and the fractional bandwidth $B_t$ has a relationship of $B_p \ge B_t$, $Bp \ge 2/3$ from the relationship with the above expression and the probe sensitivity band 10 may have a fractional bandwidth of 67% or more. As the transmit pulse P described above, for example, the following 100% amplitude modulated wave may be considered.

$$P=P'(1+\cos(2\pi f_s t))\sin(2\pi f_{pc} t)$$

In the above expression, P' indicates an amplitude of the transmit pulse P, $f_s$ indicates a modulated frequency of the transmit pulse P and $f_s=(2-B_p)f_{pc}/4$.

If the probe 20 to be used is determined, the probe sensitivity band 10 of the probe 20 is determined and the center frequency $f_{pc}$ and the fractional bandwidth $B_p$ are determined. Therefore, the condition of the first transmit pulse P1 or the second transmit pulse P2 in the ultrasound diagnosis device of the present invention is determined. The waveform generator 112 performs waveform shaping so that a pulse transmitted from the probe 20 through the transmit amplifier 111 and the transmit and receive switch 113 becomes a transmit pulse having a center frequency of $f_{pc}$ and a fractional bandwidth of $(2-B_p)/2$. By the first transmit pulse P1 or the second transmit pulse P2 transmitted as described above, it is possible to generate the sum frequency tissue harmonic echo components 420 and 421 and the difference-frequency tissue harmonic echo components 520 and 521 out of the frequency band of the probe sensitivity band 10.

As illustrated in FIG. 5, in the ultrasound diagnosis device according to the first aspect of the present invention, a ratio of the amplitude P1' of the first transmit pulse P1 and the amplitude P2' of the second transmit pulse P2 is n ($=P1'/P2'>0$) and the waveform shaping is performed by the waveform generator 112 so as to transmit the transmit pulses from the probe 20 to receive the first receive echo R1 for the first transmit pulse P1 at the first pulse sequence and the second receive echo R2 for the second transmit pulse P2 at the second pulse sequence. The first receive echo R1 and the second receive echo R2 are stored in a temporary memory provided in the signal processor 117 which is not illustrated and after completing the transmission and the reception at the first pulse sequence and the second pulse sequence, the subtraction of the first receive echo R1 and a second receive echo R2' obtained by multiplying n to the second receive echo R2 is performed to obtain the receive echo R.

Further, as illustrated in FIG. 6, in the ultrasound diagnosis device according to the second aspect of the present invention, a ratio of the amplitude P1' of the first transmit pulse P1 and the amplitude P2' of the second transmit pulse P2 is n (=P1'/P2'>0) and the second transmit pulse P2 is an inversion waveform of the first transmit pulse P1. The waveform shaping is performed by the waveform generator 112 so as to transmit the transmit pulses from the probe 20 to receive the first receive echo R1 for the first transmit pulse P1 at the first pulse sequence and the second receive echo R2 for the second transmit pulse P2 at the second pulse sequence. The first receive echo R1 and the second receive echo R2 are stored in a temporary memory provided in the signal processor 117 which is not illustrated and after completing the transmission and the reception at the first pulse sequence and the second pulse sequence, the addition of the first receive echo R1 and a second receive echo R2' obtained by multiplying n to the second receive echo R2 is performed to obtain the receive echo R.

Further, in the ultrasound diagnosis device of the first aspect and the second aspect, even though the second receive echo R2 is multiplied by n, an object of this operation is to suppress the linear tissue echo component for the fundamental wave with a ratio of intensities of the response for the first transmit pulse P1 and the response for the second transmit pulse P2 of 1:1. For example, if the operation allows the intensity ratio to be 1:1 similar to 1/n times of the first receive echo R1, is 1/n times, the operation is not limited to the examples of the above-described aspects.

In the ultrasound diagnosis device of the first aspect and the second aspect of the invention, the receive echo R obtained as described above is detected by the signal processor 117 and the output thereof is transmitted to the image processor 118. The image processor 118 constructs image data from output from the signal processor 117 and the output from the image processor 118 is displayed on the image display 3 as a video image such as a two dimensional tomographic image or a three dimensional image.

Since the tissue echo component is substantially suppressed, the video image obtained as described above may be a high CTR image in the ultrasound contrast image and sharply visualizes the vascular structure so that it is possible to provide an ultrasonic diagnosis image having a high clinical value.

Figure 7:
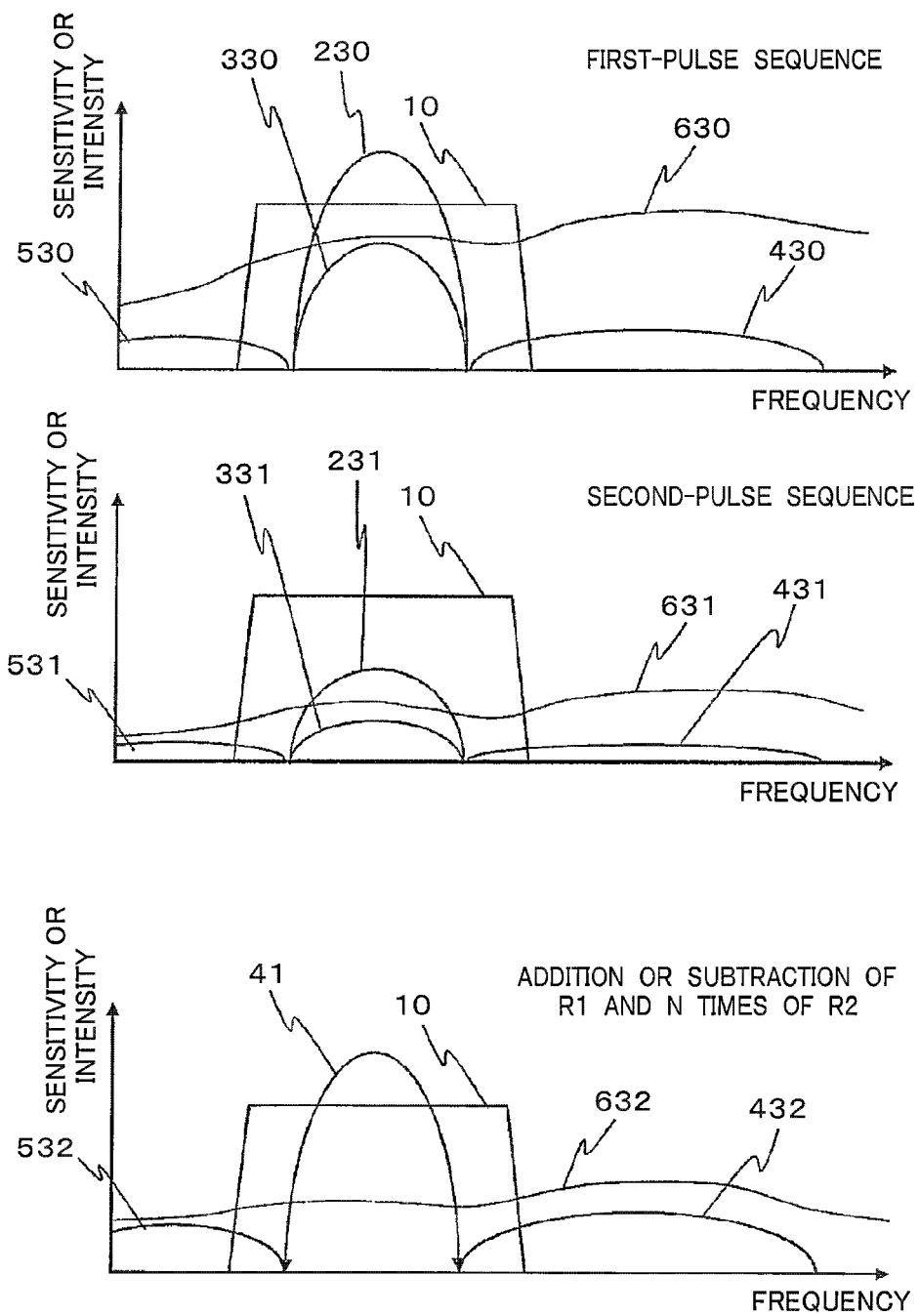
FIG. 7 is a frequency spectrum illustrating a relationship of a transmit and receive pulse band and an ultrasound probe sensitivity band at the time of ultrasound contrasting of an ultrasound diagnosis device according to third and fourth aspects of the invention.
Figure 8:
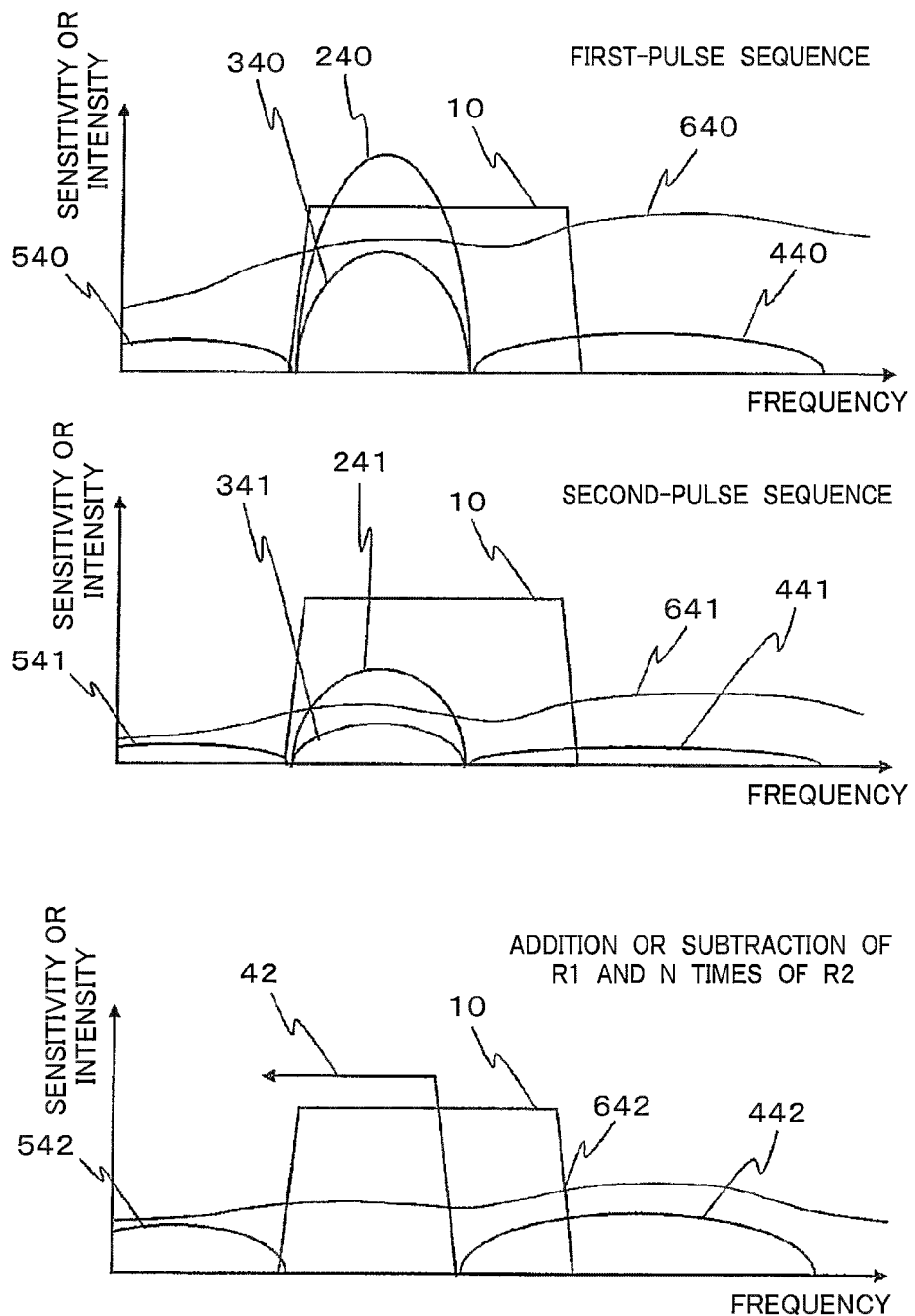
FIG. 8 is a frequency spectrum illustrating a relationship of a transmit and receive pulse band and an ultrasound probe sensitivity range at the time of ultrasound contrasting of the ultrasound diagnosis device according to a fifth aspect of the invention.

In the above embodiment, the sum and difference frequency tissue harmonic echo components are removed by the probe sensitivity band 10. However, as illustrated in FIGS. 7 to 9, the sum and difference frequency tissue harmonic echo components may be removed by the combination with a filter in accordance with the frequency bandwidth of the transmit pulse. Specifically, the sum and difference frequency tissue harmonic echo components) are generated so as to be removed from the frequency bandwidth of the transmit pulse rather than the probe sensitivity band. Further, the receive echo R may be filtered by a filter of a pass band which is equal to the frequency bandwidth of the transmit pulse which is provided in the signal processor 117 but is not illustrated.

Hereinafter, a transmit pulse condition that generates the sum and difference frequency tissue harmonic echo components so as to be removed from the frequency bandwidth of the transmit pulse will be described.

As described above, the frequency band of a sum frequency component generated by the nonlinear acoustic propagation of the first transmit pulse P1 or the second transmit pulse P2 whose frequency band is $f_{t1}$ to $f_{t2}$ is determined as a sum frequency component of all frequency components which forms the first transmit pulse P1 or the second transmit pulse P2 to be $2f_{t1}$ to $2f_{t2}$. Further, the frequency band of a transmit difference-frequency component generated by the nonlinear acoustic propagation of the first transmit pulse P1 or the second transmit pulse P2 whose frequency band is $f_{t1}$ to $f_{t2}$ is determined as a difference-frequency component of all frequency components which forms the first transmit pulse P1 or the second transmit pulse P2 to be DC to $f_{t2}-f_{t1}$. Therefore, a condition that generates the sum frequency tissue harmonic echoes 420 and 421 and the difference-frequency tissue harmonic echoes 520 and 521 out of the frequency band of the probe sensitivity band 10 is as follows:

$$f_{t1} \geq f_{t2}-f_{t1}, f_{t2} \leq 2f_{t1}$$

From the relational expression, the frequency bandwidth of the first transmit pulse P1 or the second transmit pulse P2 is $f_{t1}$ to $2f_{t1}$ at most. As long as the frequency band, which is $f_{t1}$ to $2f_{t1}$ overlaps the frequency bandwidth of the probe sensitivity band 10, the center frequency is not specifically limited. If it is represented by the fractional bandwidth $B_1$ of the transmit pulse, $$B_t = (f_{t2}-f_{t1})/f_{tc} = (2f_{t1}-f_{t1})/((f_{t1}+2f_{t1})/2) = 2/3.$$

In other words, a transmit pulse of ⅔ of the fractional bandwidth (approximately, 67%) may be the first transmit pulse P1 or the second transmit pulse P2. A frequency bands of the first transmit pulse P1 and the second transmit pulse P2 according to other three embodiments of the present invention that generate the sum or difference-frequency tissue harmonic echoes so as to be removed from the frequency band of the transmit pulse will be described with reference to FIGS. 7 to 9.

(Case when Center Frequency of Transmit Pulse is Substantially Equal to Center Frequency of Probe Sensitivity Band)

FIG. 7 is a frequency spectrum illustrating a relationship of the transmit and receive pulse band and the ultrasound probe sensitivity band in the ultrasound diagnosis device of third and fourth aspects of the present invention. In this embodiment, the center frequency of the first transmit pulse P1 or the second transmit pulse P2 is substantially equal to the center frequency of the probe sensitivity band 10 and the fractional bandwidth of the first transmit pulse P1 or the second transmit pulse P2 is ⅔ (approximately, 67%).

Frequency bands of the frequency component 230 and the frequency component 231 are provided as fundamental components of the first transmit pulse P1 at the first pulse sequence and the second transmit pulse P2 at the second pulse sequence. A frequency component of the receive echo of the first transmit pulse P1 immediately before being received by the probe 20 of the probe sensitivity band 10 is configured by a linear tissue echo component 330 for the fundamental component, a sum frequency tissue harmonic echo component 430 generated by nonlinear interaction of the frequency components 230 in the subject 30 that form the first transmit pulse P1, a difference-frequency tissue harmonic echo component 530 generated by nonlinear interaction of the frequency components 230 in the subject 30 that form the first transmit pulse P1, and a contrast echo component 630 generated by nonlinear vibration of the ultrasound contrast agent 32 excited by the first transmit pulse P1 or reflection and scattering of the first transmit pulse P1 by the ultrasound contrast agent 32. Further, a frequency component of the receive echo of the second transmit pulse P2 immediately before being received by the probe 20 is configured by a linear tissue echo component 331 for the fundamental component, a sum frequency tissue harmonic echo component 431 generated by nonlinear interaction of the frequency components 231 in the subject 30 that form the second transmit pulse P2, a difference-frequency tissue harmonic echo component 531 generated by nonlinear interaction of the frequency components 231 in the subject 30 that form the second transmit pulse P2, and a contrast echo component 631 generated by nonlinear vibration of the ultrasound contrast agent 32 excited by the second transmit pulse P2 or reflection and scattering of the second transmit pulse P2 by the ultrasound contrast agent 32.

In order to obtain a high CTR ultrasound contrast image, it is considered to efficiently capture the contrast echo components 630 and 631 and efficiently suppress or exclude the linear tissue echo components 230 and 231 or nonlinear tissue echo components 430, 530, 431, and 531. However, in this embodiment, the first transmit pulse P1 or the second transmit pulse P2 is transmitted so as not to overlap the frequency band 230 of the first transmit pulse P1 or the frequency band 231 of the second transmit pulse P2 and the nonlinear tissue echo components 430, 530, 431, and 531, which cannot be removed using a linear operation such as the pulse inversion technique, and the received signal is filtered by a band pass filter having a frequency band 41 equal to the frequency band 230 of the first transmit pulse P1 or the frequency band 231 of the second transmit pulse P2. Specifically, the first transmit pulse P1 and the second transmit pulse P2 are transmitted so as to generate the sum frequency tissue harmonic echo components 430 and 431 out of the high frequency band of the first frequency band 230 of the first transmit pulse P1 or the second frequency band 231 of the second transmit pulse P2 and predetermined difference-frequency tissue harmonic echo components 530 and 531 out of the low frequency band of the first frequency band 230 of the first transmit pulse P1 or the second frequency band 231 of the second transmit pulse P2 and the sum or difference-frequency tissue harmonic echo components are filtered and removed from the obtained receive echo R.

In the ultrasound diagnosis device of the third aspect of the invention, the second transmit pulse P2 has an amplitude which is equal to that of a transmit pulse which is 1/n times (n>0) of an amplitude of the first transmit pulse P1 and as illustrated in FIG. 5, the receive echo R is obtained by the subtraction of the first receive echo R1 and the second receive echo R2'. Further, in the ultrasound diagnosis device according to the fourth aspect of the invention, the second transmit pulse P2 is equal to a transmit pulse obtained by inversing the first transmit pulse P1 (phase is rotated at 180 degrees) with an amplitude obtained by multiplying 1/n (n>0) to the amplitude of the first transmit pulse P1 and as illustrated in FIG. 6, the receive echo R is obtained by the addition of the first receive echo R1 and the second receive echo R2'.

The receive echo R obtained as described above is composed of components in which any of the linear tissue echo components 330 and 331 are removed by the linear operation and the sum frequency tissue harmonic echo component 432, the difference-frequency tissue harmonic echo component 532, and the contrast echo component 632 are filtered in the probe sensitivity band 10. However, in the frequency band corresponding to the frequency band 230 or 231 of the first transmit pulse P1 or the second transmit pulse P2, only the contrast echo component 632 is present. By filtering the contrast echo component 632 by the band pass filter having a signal pass band 41, it is possible to obtain a high CTR received signal. Simultaneously, it is possible to suppress electric noise because the band limitation by the band pass filter is applied also in the probe sensitivity band 10. Therefore, the SN ratio with respect to the electric noise may be increased and a high CTR ultrasound contrast image may be obtained.

(Case when Lower Limit Frequency of Transmit Pulse is Substantially Equal to Lower Limit Frequency of Probe Sensitivity Band)

FIG. 8 is a frequency spectrum illustrating a relationship of a transmit and receive pulse band and an ultrasound probe sensitivity band in the ultrasound diagnosis device according to a fifth aspect of the invention. In this embodiment, the lower limit frequency of the first transmit pulse P1 or the second transmit pulse P2 is substantially equal to the lower limit frequency of the probe sensitivity band 10 and the fractional bandwidth of the first transmit pulse P1 or the second transmit pulse P2 is $\frac{2}{3}$ (approximately 67%).

Frequency bands of the frequency component 240 and the frequency component 241 are provided as fundamental components of the first transmit pulse P1 at the first pulse sequence and the second transmit pulse P2 at the second pulse sequence. A frequency component of the receive echo of the first transmit pulse P1 immediately before being received by the probe 20 of the probe sensitivity band 10 is configured by a linear tissue echo component 340 for the fundamental component, a sum frequency tissue harmonic echo component 440 generated by nonlinear interaction of the frequency components 240 in the subject 30 that form the first transmit pulse P1, a difference-frequency tissue harmonic echo component 540 generated by nonlinear interaction of the frequency component 240 in the subject 30 that form the first transmit pulse P1, and a contrast echo component 640 generated by nonlinear vibration of the ultrasound contrast agent 32 excited by the first transmit pulse P1 or reflection and scattering of the first transmit pulse P1 by the ultrasound contrast agent 32. Further, a frequency component of the receive echo of the second transmit pulse P2 immediately before being received by the probe 20 is configured by a linear tissue echo component 341 for the fundamental component, a sum frequency tissue harmonic echo component 441 generated by nonlinear interaction of the frequency components 241 in the subject 30 that form the second transmit pulse P2, a difference-frequency tissue harmonic echo component 541 generated by nonlinear interaction of the frequency component 241 in the subject 30 that form the second transmit pulse P2, and a contrast echo component 641 generated by nonlinear vibration of the ultrasound contrast agent 32 excited by the second transmit pulse P2 or reflection and scattering of the second transmit pulse P2 by the ultrasound contrast agent 32.

In order to obtain a high CTR ultrasound contrast image, it is considered to efficiently capture the contrast echo components 640 and 641 and efficiently suppress or exclude the linear tissue echo components 240 and 241 or nonlinear tissue echo components 440, 540, 441, and 541. In this embodiment, the first transmit pulse P1 or the second transmit pulse P2 is transmitted so as not to overlap the frequency band 240 of the first transmit pulse P1 or the frequency band 241 of the second transmit pulse P2 and the nonlinear tissue echo components 440, 540, 441, and 541, which cannot be removed using a linear operation such as the pulse inversion technique, and the received signal is filtered by a low pass filter having a signal pass band 42 in which the upper limit frequency of the frequency band 240 of the first transmit pulse P1 or the frequency band 241 of the second transmit pulse P2 is a cut off frequency. Specifically, the first transmit pulse P1 and the second transmit pulse P2 are transmitted so as to generate the sum frequency tissue harmonic echo components 440 and 441 out of the high frequency band of the frequency band 240 of the first transmit pulse P1 or the frequency band 241 of the second transmit pulse P2 and predetermined difference-frequency tissue harmonic echo components 540 and 541 out of the low frequency band of the first frequency band 240 of the first transmit pulse P1 or the frequency band 241 of the second transmit pulse P2, and the sum or difference-frequency tissue harmonic echo component is removed from the obtained receive echo R by filtering or band limitation by the probe sensitivity band 10. Further, instead of the low pass filter, a band pass filter having the same signal pass band as the frequency band 240 of the first transmit pulse P1 or the frequency band 241 of the second transmit pulse P2 may be used for filtering.

In the ultrasound diagnosis device according to the fifth aspect of the invention, the second transmit pulse P2 is equal to a transmit pulse having an amplitude which is 1/n times (n>0) of an amplitude of the first transmit pulse P1. Similarly to the third or fourth aspect of the invention, the receive echo R is obtained by the subtraction processing of the first receive echo R1 and the second receive echo R2' if the first transmit pulse P1 and the second transmit pulse P2 have the same phase. In contrast, if the first transmit pulse P1 and the second transmit pulse P2 have inverse phases, the receive echo R is obtained by the addition processing of the first receive echo R1 and the second receive echo R2'.

From the receive echo R obtained as described above, any of the linear tissue echo components 340 and 341 are removed by the linear operation and the difference-frequency tissue harmonic echo component 542 is removed by the band limitation of the probe sensitivity band 10. Therefore, the receive echo R is composed by components obtained by filtering the sum frequency tissue harmonic echo component 442 and the contrast echo component 632 in the probe sensitivity band 10. However, in the frequency band corresponding to the frequency band 240 or 241 of the first transmit pulse P1 or the second transmit pulse P2, only the contrast echo component 642 is present. By filtering the contrast echo component 642 by the low pass filter having a signal pass band 42, it is possible to obtain a high CTR received signal. Simultaneously, it is possible to suppress electric noise because the band limitation by the low pass filter is applied also in the probe sensitivity band 10. Therefore, the SN ratio with respect to the electric noise may be increased and a high CTR ultrasound contrast image may be obtained. Further, the contrast echo signal is obtained at the low frequency band side of the probe sensitivity band 10 so that an ultrasound contrast image having an excellent depth penetration may be obtained.

(Case when Upper Limit Frequency of Transmit Pulse is Substantially Equal to Upper Limit Frequency of Probe Sensitivity Band)

FIG. 9 is a frequency spectrum illustrating a relationship of a transmit and receive pulse band and an ultrasound probe sensitivity band in the ultrasound diagnosis device according to a sixth aspect of the invention. In this embodiment, the upper limit frequency of the first transmit pulse P1 or the second transmit pulse P2 is substantially equal to the upper limit frequency of the probe sensitivity band 10 and the fractional bandwidth of the first transmit pulse P1 or the second transmit pulse P2 is ⅔ (approximately 67%).

Frequency bands of the frequency component 250 and the frequency component 251 are provided as fundamental components of the first transmit pulse P1 at the first pulse sequence and the second transmit pulse P2 at the second pulse sequence. A frequency component of the receive echo of the first transmit pulse P1 immediately before being received by the probe 20 of the probe sensitivity band 10 is configured by a linear tissue echo component 350 for the fundamental component, a sum frequency tissue harmonic echo component 450 generated by nonlinear interaction of the frequency components 250 in the subject 30 that form the first transmit pulse P1, a difference-frequency tissue harmonic echo component 550 generated by nonlinear interaction of the frequency components 250 in the subject 30 that form the first transmit pulse P1, and a contrast echo component 650 generated by nonlinear vibration of the ultrasound contrast agent 32 excited by the first transmit pulse P1 or reflection and scattering of the first transmit pulse P1 by the ultrasound contrast agent 32. Further, a frequency component of the receive echo of the second transmit pulse P2 immediately before being received by the probe 20 is configured by a linear tissue echo component 351 for the fundamental component, a sum frequency tissue harmonic echo component 451 generated by nonlinear interaction of the frequency components 251 in the subject 30 that form the second transmit pulse P2, a difference-frequency tissue harmonic echo component 551 generated by nonlinear interaction of the frequency components 251 in the subject 30 that form the second transmit pulse P2, and a contrast echo component 651 generated by nonlinear vibration of the ultrasound contrast agent 32 excited by the second transmit pulse P2 or reflection and scattering of the second transmit pulse P2 by the ultrasound contrast agent 32.

In order to obtain a high CTR ultrasound contrast image, it is considered to efficiently capture the contrast echo components 650 and 651 and efficiently suppress or exclude the linear tissue echo components 250 and 251 or nonlinear tissue echo components 450, 550, 451, and 551. In this embodiment, the first transmit pulse P1 or the second transmit pulse P2 is transmitted so as not to overlap the frequency band 250 of the first transmit pulse P1 or the frequency band 251 of the second transmit pulse P2 and the nonlinear tissue echo components 450, 550, 451, and 551, which cannot be removed using a linear operation such as the pulse inversion technique, and the received signal is filtered by a high pass filter having a signal pass band 43 in which the lower limit frequency of the frequency band 250 of the first transmit pulse P1 or the frequency band 251 of the second transmit pulse P2 is a cut off frequency. Specifically, the first transmit pulse P1 and the second transmit pulse P2 are transmitted so as to generate the sum frequency tissue harmonic echo components 450 and 451 out of the high frequency band of the frequency band 250 of the first transmit pulse P1 or the frequency band 251 of the second transmit pulse P2 and predetermined difference-frequency tissue harmonic echo components 550 and 551 out of the low frequency band of the frequency band 250 of the first transmit pulse P1 or the frequency band 251 of the second transmit pulse P2. The sum or difference-frequency tissue harmonic echo component is removed from the obtained receive echo R by filtering or band limitation by the probe sensitivity band 10. Further, instead of the high pass filter, a band pass filter having the same signal pass band as the frequency band 250 of the first transmit pulse P1 or the frequency band 251 of the second transmit pulse P2 may be used for filtering.

In the ultrasound diagnosis device according to the sixth aspect of the invention, the second transmit pulse P2 is equal to a transmit pulse having an amplitude which is 1/n times (n>0) of an amplitude of the first transmit pulse P1. Similarly to the third or fourth aspect of the invention, the receive echo R is obtained by the subtraction processing of the first receive echo R1 and the second receive echo R2' if the first transmit pulse P1 and the second transmit pulse P2 have the same phase. In contrast, if the first transmit pulse P1 and the second transmit pulse P2 have inverse phases, the receive echo R is obtained by the addition processing of the first receive echo R1 and the second receive echo R2'.

From the receive echo R obtained as described above, any of the linear tissue echo components 350 and 351 are removed by the linear operation and the sum frequency tissue harmonic echo component 452 is removed by the band limitation of the probe sensitivity band 10. Therefore, the receive echo R is composed of components obtained by filtering the difference-frequency tissue harmonic echo component 552 and the contrast echo component 652 in the probe sensitivity band 10. However, in the frequency band corresponding to the frequency band 250 or 251 of the first transmit pulse P1 or the second transmit pulse P2, only the contrast echo component 652 is present. By filtering the contrast echo component 652 by the high pass filter having a signal pass band 43, it is possible to obtain a high CTR received signal. Simultaneously, it is possible to suppress electric noise because the band limitation by the high pass filter is applied also in the probe sensitivity band 10. Therefore, the SN ratio with respect to the electric noise may be increased and a high CTR ultrasound contrast image may be obtained. Further, the contrast echo signal is obtained at the high frequency band side of the probe sensitivity band 10 so that an ultrasound contrast image having an excellent spatial resolution may be obtained.

Figure 3:
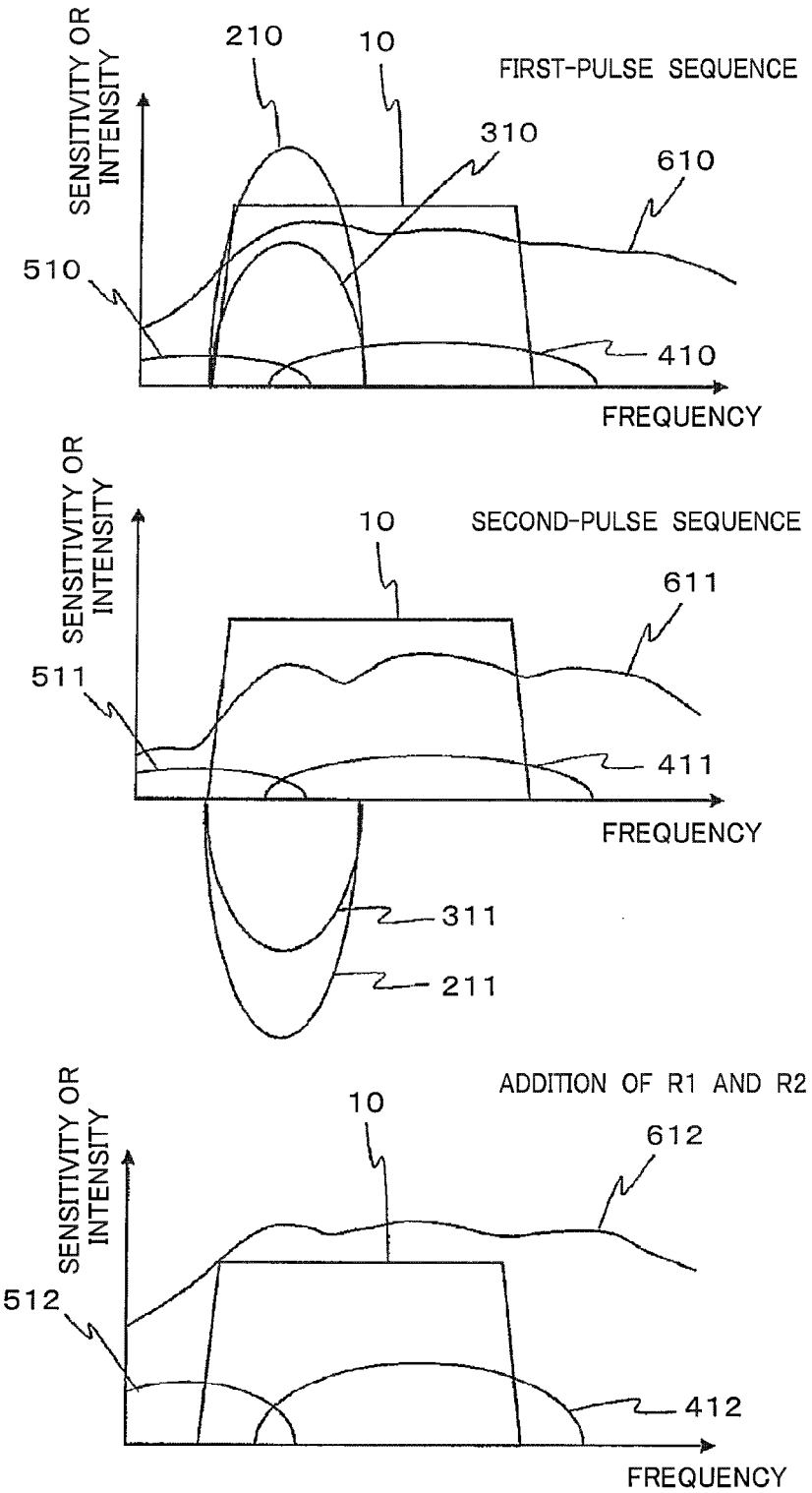
FIG. 3 is a frequency spectrum illustrating a relationship of a transmit and receive pulse band and an ultrasound probe sensitivity band at the time of ultrasound contrasting of an ultrasound diagnosis device of another related art.

In order to check of the effect of the high CTR by the ultrasound diagnosis device according to the present invention described above, an ultrasound pulse response simulation of the ultrasound contrast agent based on a Keller-Miksis equation which considers a compressibility of surrounding fluid and nonlinear acoustic propagation simulation based on a KZK equation (Khokhlov-Zabolotskaya-Kuznetsov equation) are performed. A signal component represented by the contrast echo is evaluated by the former simulation and a noise component represented by the tissue echo is evaluated by the latter simulation to compare the CTRs obtained by the related art illustrated in FIG. 3 and the method of the present invention illustrated in FIG. 4. The result thereof will be described below.

First, the probe sensitivity band is defined as if a filter in a Hanning window is created under the assumption of a frequency band in which the center frequency is 3 MHz and a fractional bandwidth is 100%. Further, in the related art, as a transmit pulse condition, it is assumed that the center frequency is 2 MHz and a wave number of a hanning weight is 4 (fractional bandwidth 50%), and a maximum sound pressure amplitude is 212 kPa. In contrast, in the present invention, as a transmit pulse condition, it is assumed that the center frequency is 3 MHz and a wave number of a hanning weight is 4 (fractional bandwidth 50%), a maximum sound pressure amplitude of the first transmit pulse P1 is 520 kPa, a maximum sound pressure amplitude of the second transmit pulse P2 is 260 kPa, and the phase of the first transmit pulse P1 is equal to that of the second transmit pulse P2. The above condition is assumed such that a value of a mechanical index MI which is used as an index of a safety of the ultrasound wave for a biological body is the same in the method according to the related art and the method according to the present invention. In other words, MI is defined as $MI=P_0/\sqrt{f_c}$ from the center frequency $f_c$ (MHz) of the transmit pulse and a maximum sound pressure amplitude $P_0$ (MPa) of a negative pressure and MI=0.3 both in the method according to the related art and the method according to the present invention under the above-mentioned condition.

As the ultrasound contrast agent, sonazoid is assumed. As for the sonazoid, it is assumed that a radius is 1 μm, a shell thickness is 10 nm, a shell shear modulus is 50 MPa, a shell viscous coefficient is 0.8 Pa·s. Further, as for gas in the contrast agent, it is assumed that a density is 1.61 kg/m$^3$, a thermal conductivity is $26.2 \times 10^{-3}$ W/mk, a thermal capacity is 1007 J/kgK and a ratio of specific heats is 1.4. As for the surrounding fluid, a blood is assumed (a density is 1,025 kg/m$^3$, a viscous coefficient is $4 \times 10^{-3}$ Pa·S, and a speed of sound is 1,570 m/s). Under this condition, in the method according to the related art, as for each of the first transmit pulse P1 and the second transmit pulse P2, a response for one ultrasound contrast agent is obtained by a simulation and after performing an addition processing of the response waveform for the first transmit pulse P1 and the response waveform for the second transmit pulse P2, the first transmit pulse P1 and the second transmit pulse P2 are filtered under the condition of the above-mentioned probe sensitivity band to obtain a contrast echo component. In contrast, in the method according to the present invention, as for each of the first transmit pulse P1 and the second transmit pulse P2, a response for one ultrasound contrast agent is obtained by the simulation and after performing a subtraction processing of the response waveform for the first transmit pulse P1 and a waveform obtained by increasing two times the response waveform for the second transmit pulse P2, the first transmit pulse P1 and the second transmit pulse P2 are filtered under the condition of the above-mentioned probe sensitivity band to obtain a contrast echo component.

Further, in the nonlinear acoustic propagation simulation, a uniform acoustic medium which is similar to the physical property of the biological body is assumed and it is assumed that the speed of sound is 1,540 m/s, the density is 1,000 kg/m$^3$, a nonlinear parameter B/A is 7, and a frequency dependent absorption coefficient is 0.7 (dB/cm/MHz). In this nonlinear acoustic propagation simulation, two dimensional plane of the acoustic medium is assumed and a sound pressure waveform at a focal point is obtained by the simulation with an aperture of the probe of 10 mm and a focal distance of 80 mm. In contrast, in the method of the present invention, an aperture amplitude apodization of the first transmit pulse P1 and the second transmit pulse P2, as illustrated in FIG. 10, uses all apertures so that a sound pressure of the second transmit pulse P2 is half of a sound pressure of the first transmit pulse P1. With this condition, in the method of the related art, the nonlinear acoustic propagation waveform for each of the first transmit pulse P1 and the second transmit pulse P2 is obtained by the simulation and after performing an addition processing of a waveform for the first transmit pulse P1 and a waveform for the second transmit pulse P2, the first transmit pulse P1 and the second transmit pulse P2 are filtered under the condition of the above-mentioned probe sensitivity band to obtain a nonlinear tissue echo component. In contrast, according to a method of the present invention, after performing the subtraction processing of the waveform of the first transmit pulse P1 and a waveform obtained by increasing two times the waveform of the second transmit pulse P2, the first transmit pulse P1 and the second transmit pulse P2 are filtered under the condition of the above-mentioned probe sensitivity band to obtain a nonlinear tissue echo component.

Hereinafter, a result of the simulation will be described.

Figure 13:
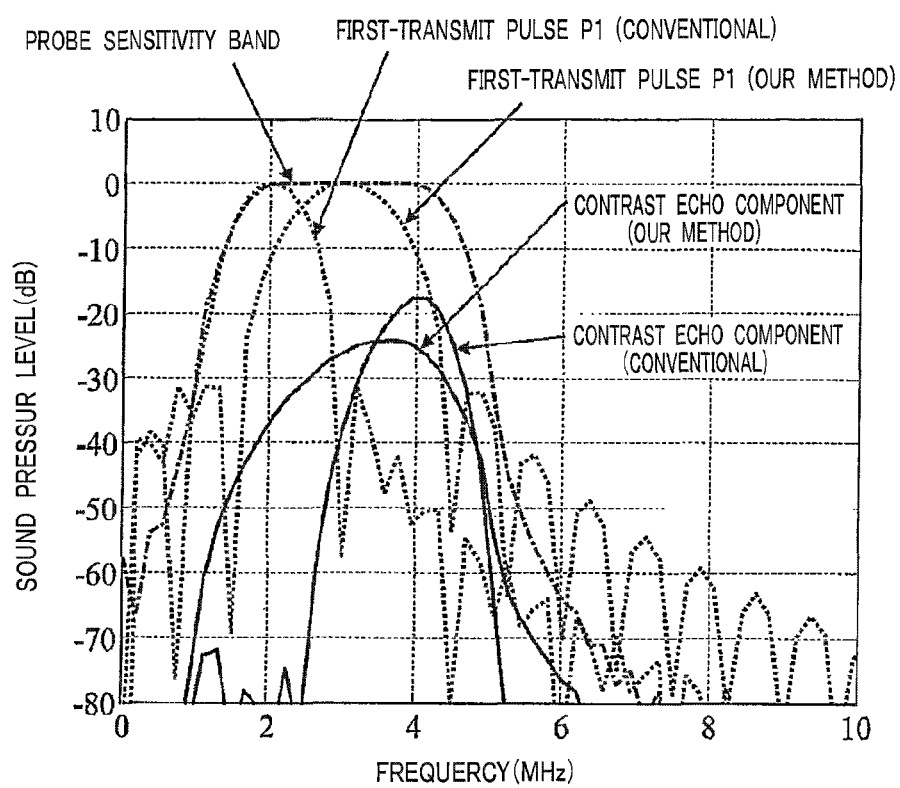
FIG. 13 is a frequency dependence view illustrating a contrast echo component by simulation.

First, a response of the ultrasound contrast agent will be described with reference to FIG. 13. FIG. 13 is a frequency dependence view illustrating a contrast echo component of the ultrasound contrast agent according to methods in the related art and the present invention. In FIG. 13, a frequency band (normalized with a maximum sensitivity) corresponding to the probe sensitivity band and frequency bands (each normalized with a maximum strength) corresponding to the first transmit pulses P1 in the methods of the related art and the present invention are illustrated. Since a sound pressure level for a response for one ultrasound contrast agent is very low, for the convenience of the display, the sound pressure level for the response for the ultrasound contrast agent is increased by 140 dB to be displayed. From this result, it is appreciated that the contrast echo component in the method of the present invention has slightly lower sound pressure level than that in the method of the related art, but the contrast echo component is generated all over the probe sensitivity band. Specifically, it is understood that the signal is significantly distributed toward the low frequency and formed of very broad band signal. In other words, according to the method of the present invention, the contrast echo component becomes broader, which improves the spatial resolution and the depth penetration of the ultrasound contrast image.

Figures 14, 15:
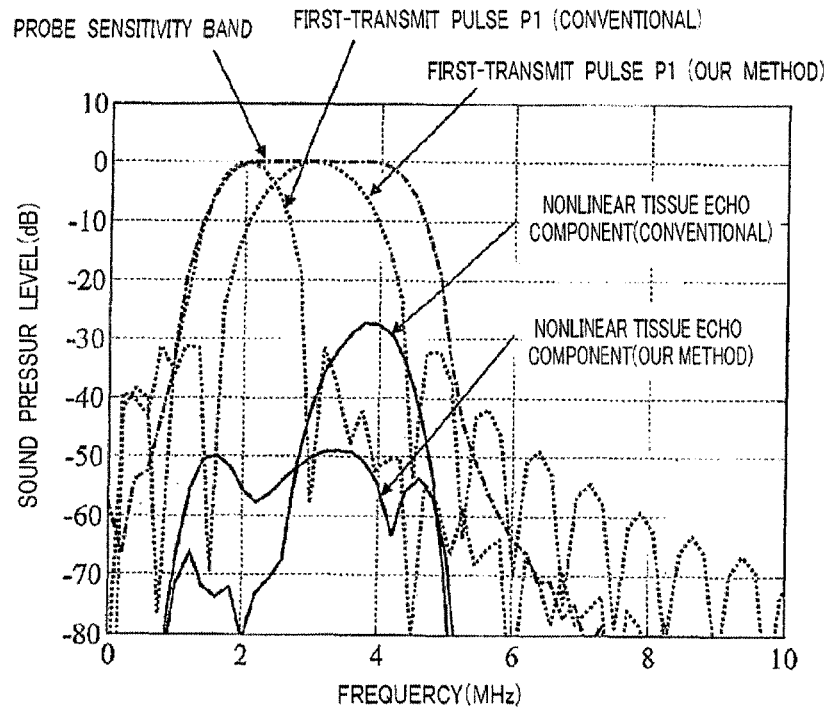
FIG. 14 is a frequency dependence view illustrating a nonlinear tissue echo component by simulation.
FIG. 15 is a CTR comparison table for a simulation result.

Next, a nonlinear tissue echo component obtained by the nonlinear acoustic propagation simulation will be described with reference to FIG. 14. FIG. 14 is a frequency dependence view illustrating nonlinear tissue echo components in methods according to the related art and the present invention. In FIG. 14, a frequency band (normalized with a maximum sensitivity) corresponding to the probe sensitivity band and frequency bands (each normalized with a maximum strength) corresponding to the first transmit pulses P1 in the methods of the related art and the present invention are illustrated. From this result, it is understood that a sound pressure level of the nonlinear tissue echo component in the method of the present invention is suppressed to be much smaller than that in the related art. In other words, in the method of the related art, since a region corresponding to a second harmonic wave of the transmit pulse is used to form an image, the nonlinear tissue echo component of the second harmonic area inevitably becomes larger. In contrast, in the method of the present invention, the first transmit pulse P1 and the second transmit pulse P2 are formed so as to generate a region corresponding to the second harmonic wave (sum frequency component) out of the high frequency band of the probe sensitivity band and a difference-frequency component generated region out of the low frequency band of the probe sensitivity band. Therefore, it is possible to entirely remove the nonlinear tissue echo component and obtain a high CTR ultrasound contrast image.

In order to find an effect for the CTR of the method of the present invention as compared with the method of the related art, from the above-mentioned simulation result, an envelope maximum amplitude of a waveform of the contrast echo component and an envelope maximum amplitude of a waveform of the nonlinear tissue echo component according to the methods in the related art and the present invention are compared and the result is illustrated in FIG. 15. As illustrated in FIG. 15, if the contrast echo components are compared for the methods of the related art and the present invention, the envelope maximum amplitudes are −157.36 dB in the method of the related art and −162.06 dB in the method of the present invention. The contrast echo component, which becomes a signal in the ultrasound contrast image, is by 4.7 dB lower in the method of the present invention than in the method of the related art. Further, if the nonlinear tissue echo components are similarly compared, the nonlinear tissue echo component are −25.65 dB in the method of the related art and −46.38 dB in the method of the present invention. Therefore, the nonlinear tissue echo component which becomes noise in the ultrasound contrast image is by 20.7 dB lower in the method of the present invention than in the method of the related art. Accordingly, if the CTRs are compared using the relative comparison of both the signal and the noise, the method of the present invention has the improved CTR as follows:

−4.7 dB−(−20.7 dB)=16.0 dB.

Therefore, the high CTR effect according to the method of the present invention is confirmed.

A specific example of the operation at the time of ultrasound contrast diagnosis performed with the above-described configuration and under the condition will be described with reference to the drawings.

Figure 12:
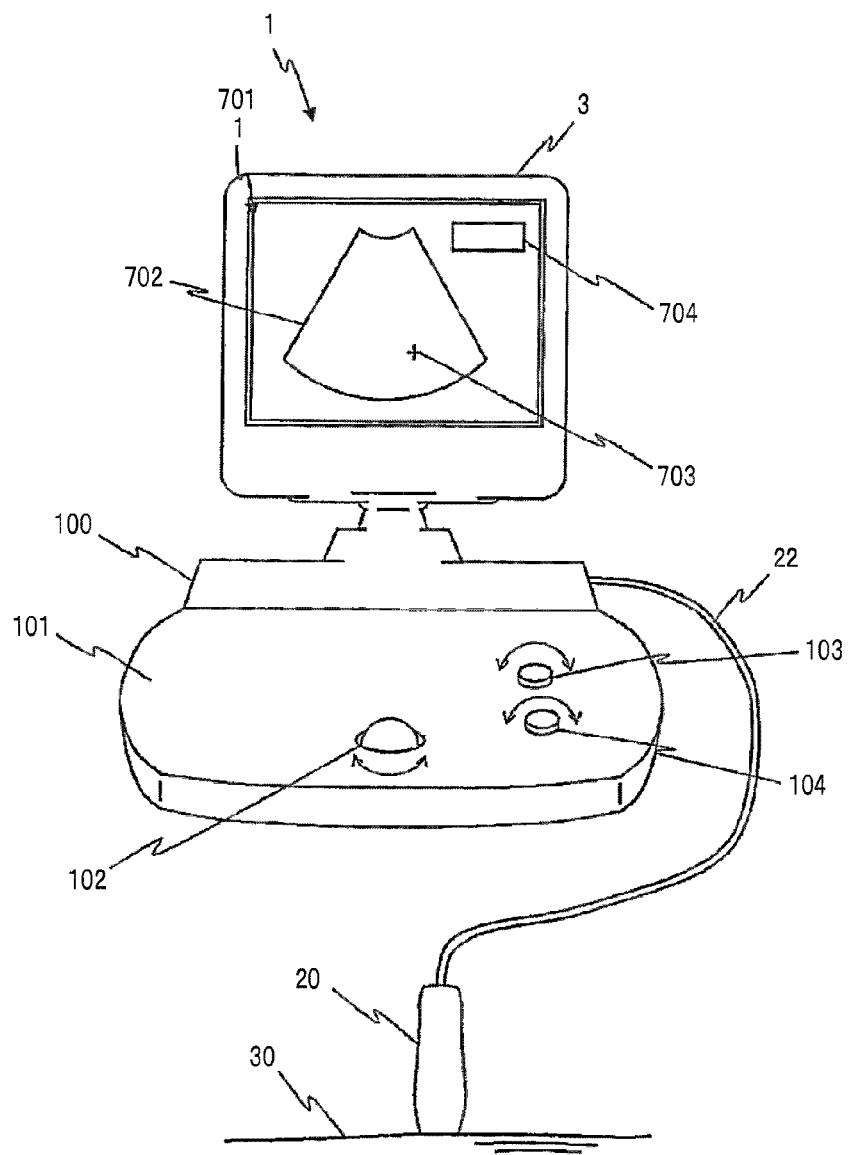
FIG. 12 is a conceptual view of an operation illustrating an embodiment of the ultrasound diagnosis device according to the invention.

FIG. 12 is an operational conceptual view illustrating an embodiment of the ultrasound diagnosis device according to the invention. The ultrasound diagnosis device 1 includes a main body 100 of the device, a cable 22, a probe 20, an image display 3, and a manipulation panel 101 that allows a user to input capturing conditions. Before intravenously injecting the ultrasound contrast agent, if an operator touches the subject 30 with the probe 20, a captured image 702 is displayed on a display screen 701 of the image display 3. In this case, a position of the representative area is indicated by a marker 703 so that the user manipulates the manipulation panel 101 to select the representative area. On the display screen 701, brightness information in the representative area of the captured image 702 indicated by the marker 703 is displayed on a number display 704. In the manipulation panel 101, transmit waveform adjusting units 103 and 104 are manipulated to adjust the center frequency or the fractional bandwidth of the first transmit pulse P1 or the second transmit pulse P2 to change the transmit pulse waveform. In the manipulation panel 101, an adjusting unit for an amplitude ratio n of the first receive echo R1 and the second receive echo R2 may be provided.

First, the user manipulates the marker 703 for the captured image of the subject 30 before intravenously injecting the ultrasound contrast agent using a trackball 102 and display a brightness of the tissue echo on the number display 704. If the tissue echo is not sufficiently suppressed, the user manipulates the transmit waveform adjusting units 103 and 104 to adjust the transmit pulse so as to lower the brightness to be displayed on the number display 704. By doing this, it is possible to set an optimal transmit pulse condition for the subject 30 so as to sufficiently suppress or exclude the tissue echo before obtaining the ultrasound contrast image. After determining the condition where the tissue echo is sufficiently suppressed, the ultrasound contrast agent is intravenously injected into the subject 30 to capture the ultrasound contrast image. Further, at the time of capturing the ultrasound contrast image, the transmit waveform adjusting units 103 and 104 are manipulated to search for better capturing conditions.

By the operation of the ultrasound diagnosis device as described above, an optimal CTR ultrasound contrast image may be obtained and a high quality diagnosis image may be obtained by fixing the setting condition even when the patient-dependency is strong.

REFERENCE SIGNS LIST

1 Ultrasound diagnosis device
2 External interface
3 Image display
10 Probe sensitivity band
20 Probe
21a to 21z Electro-acoustic conversion element
22 Cable
30 Subject
31 Blood vessel
32 Ultrasound contrast agent 41 Band pass filter signal pass band
42 Low pass filter signal pass band
43 High pass filter signal pass band
100 Main body
101 Manipulation panel
102 Trackball
103, 104 Transmit waveform adjusting unit
110 Main body component
111 Transmit amplifier
112 Waveform generator
113 Transmit and receive (T/R) switch
114 Receive amplifier
115 A/D converter
116 Receive delay circuit
117 Signal processor
118 Image processor
120 Controller
200, 210, 211, 220, 221, 230, 231, 240, 241, 250, 251 Frequency component of transmit pulse
300, 310, 311, 320, 321, 330, 331 Linear tissue echo component
400, 410 to 412, 420 to 422, 430 to 432, 440 to 442, 450 to 452 Sum frequency tissue harmonic echo component
500, 510 to 512, 520 to 522, 530 to 532, 540 to 542, 550 to 552 Difference-frequency tissue harmonic echo component
600, 610 to 612, 620 to 622, 630 to 632, 640 to 642, 650 to 652 Contrast echo component
701 Display screen
702 Captured image
703 Marker
704 Number display

The invention claimed is:

1. An ultrasound device, comprising:
a transmitter that includes a waveform generator and an amplifier and generates a transmit signal;
an ultrasound probe that converts the transmit signal generated from the transmitter into an acoustic signal to transmit an ultrasound transmit pulse to a subject and receives a reflected echo from the subject; and
a signal processor that performs a signal processing of the received reflected echo,
wherein the transmitter generates the transmit signal so as to make a lower limit frequency of sum frequency components generated in the subject by the nonlinear interaction of acoustic waves of frequency components that form the transmit pulse and an upper limit frequency of a sensitivity frequency band of the ultrasound probe substantially equal, and so as to make an upper limit frequency of difference frequency components generated in the subject by the nonlinear interaction of acoustic waves of frequency components that form the transmit pulse and a lower limit frequency of a sensitivity frequency band of the ultrasound probe substantially equal, and
the signal processor suppresses a linear echo from the subject in the sensitivity frequency band of the ultrasound probe.

2. The ultrasound device according to claim 1,
wherein the ultrasound probe has a sensitivity frequency band of a center frequency $f_{pc}$ and a fractional bandwidth of $B_p$ and receives a first receive echo R1 which transmits and receives a first transmit pulse P1 which is a pulse having a center frequency which is equal to the center frequency $f_{pc}$ and a fractional bandwidth of $(2-B_p)/2$ and
a second receive echo R2 that transmits and receives a second transmit pulse P2 which is a pulse obtained by multiplying 1/n where n>0, to an amplitude of the first transmit pulse P1 on the same scanning line as the first transmit pulse P1 from the ultrasound probe, and
the signal processor subtracts the first receive echo R1 and a receive echo R2' obtained by multiplying n to the amplitude of the second receive echo R2 to obtain a receive echo R on the scanning line.

3. The ultrasound device according to claim 2, wherein the sensitivity frequency band of the ultrasound probe is an ultrasound frequency band which is transmittable and receivable by the ultrasound probe.

4. The ultrasound device according to claim 2, wherein the n is represented by m-th power of 2 when m is an integer.

5. The ultrasound device according to claim 2, wherein the n is 2.

6. The ultrasound device according to claim 2, wherein when an amplitude of the first transmit pulse P1 is $P_0$, an amplitude of the second transmit pulse P2 is $P_0/2$.

7. The ultrasound device according to claim 2, wherein conditions of the first transmit pulse P1 and the second transmit pulse P2 are determined based on the center frequency $f_{pc}$ and the fractional bandwidth $B_p$ obtained from the sensitivity frequency band of the ultrasound probe.

8. The ultrasound device according to claim 1, wherein the sensitivity frequency band of the ultrasound probe is an ultrasound frequency band which is transmittable and receivable by the ultrasound probe.

9. An ultrasound device, comprising:
a transmitter that includes a waveform generator and an amplifier and generates a transmit signal;
an ultrasound probe that converts the transmit signal generated from the transmitter into an acoustic signal to transmit an ultrasound transmit pulse to a subject and receives a reflected echo from the subject; and
a signal processor that performs a signal processing of the received reflected echo,
wherein the transmitter generates the transmit signal so as to make a lower limit frequency of sum frequency components generated in the subject by the nonlinear interaction of acoustic waves of frequency components that form the transmit pulse and an upper limit frequency of a sensitivity frequency band of the transmit pulse substantially equal, and so as to make an upper limit frequency of difference frequency components generated in the subject by the nonlinear interaction of acoustic waves of frequency components that form the transmit pulse and a lower limit frequency of a sensitivity frequency band of the transmit pulse substantially equal, and
the signal processor extracts a band component corresponding to the frequency band of the transmit pulse from the reflected echo received by the ultrasound probe, and suppresses a linear echo from the subject in the sensitivity frequency band of the transmit pulse.

* * * * *